(12) United States Patent
Bae et al.

(10) Patent No.: US 11,767,541 B1
(45) Date of Patent: Sep. 26, 2023

(54) ADENO-ASSOCIATED VIRUS COMPLEX WITH IMPROVED EXPRESSION OF RUNX3 GENE AND USES FOR PREVENTING OR TREATING KRAS MUTATED LUNG CANCER

(71) Applicant: GENECRAFT INC., Cheongju-si (KR)

(72) Inventors: Suk Chul Bae, Cheongju-si (KR); You Soub Lee, Cheongju-si (KR); Xinzi Chi, Cheongju-si (KR); Ja Yeol Lee, Cheongju-si (KR)

(73) Assignee: GENECRAFT, INC., Cheongju-si (KR)

( * ) Notice: Subject to any disclaimer, the term of this patent is extended or adjusted under 35 U.S.C. 154(b) by 0 days.

(21) Appl. No.: 18/190,561

(22) Filed: Mar. 27, 2023

(51) Int. Cl.
*C12N 15/113* (2010.01)
*C12N 15/86* (2006.01)
*A61P 35/00* (2006.01)

(52) U.S. Cl.
CPC .............. *C12N 15/86* (2013.01); *A61P 35/00* (2018.01); *C12N 15/113* (2013.01); *C12N 2750/14143* (2013.01)

(58) Field of Classification Search
None
See application file for complete search history.

(56) References Cited

PUBLICATIONS

Zhou, et al. (2017) "Deletion of the B-B' and C-C' regions of inverted terminal repeats reduces rAAV productivity but increases transgene expression", 7: e5432, 13 pages. (Year: 2017).*
Sayroo, et al. (2015) "Development of novel AAV serotype 6 vectors with selective tropism for human cancer cells", Gene Therapy, 23: 18-25. (Year: 2015).*
Chen, et al. (2014) "Role of RUNX3 in Suppressing Metastasis and Angiogenesis of Human Prostate Cancer", PLOS One, 9(1): e86917, 11 pages. (Year: 2014).*
Lee, et al. (2010) "Runx3 is required for the differentiation of lung epithelial cells and suppression of lung cancer", Oncogene, 29: 3349-61. (Year: 2010).*
Gonçalves, M., "Adeno-associated virus: from defective virus to effective vector," *Virology Journal*, 2(43):17 pgs. (2005).

* cited by examiner

*Primary Examiner* — Robert M Kelly
(74) *Attorney, Agent, or Firm* — Crowell & Moring LLC

(57) ABSTRACT

Provided is an adeno-associated virus (AAV) complex for expression of an RUNX3 gene including an asymmetrically modified inverted terminal repeat (ITR). The AAV complex has asymmetric ITRs in which one of the two ITRs is modified, thereby increasing self-replication efficiency in host cells and increasing expression efficiency of a delivered gene, and therefore, compared to existing AAV complexes, the AAV complex has an advantage of improved productivity and gene expression efficiency.

14 Claims, 16 Drawing Sheets

Specification includes a Sequence Listing.

ADENO-ASSOCIATED VIRUS COMPLEX WITH IMPROVED EXPRESSION OF RUNX3 GENE AND USES FOR PREVENTING OR TREATING KRAS MUTATED LUNG CANCER

REFERENCE TO APPENDIX [CD ROM/SEQUENCE LISTING]

The instant application contains a Sequence Listing XML which has been submitted electronically in XML format and is hereby incorporated by reference in its entirety. Said XML copy, created on Mar. 14, 2023, is named "PX067023US_SEQ Lisitng.xml" and is 24,997 bytes in size.

BACKGROUND

The present disclosure relates to an adeno-associated virus complex with improved expression of RUNX3, and uses for preventing or treating KRAS mutated lung cancer.

A KRAS gene is a substance involved in a function of an enzyme protein of GTP, which plays an important role in a signal transduction system related to cell differentiation, proliferation and survival. When a signal is transmitted in a cell unit, a KRAS protein binds to GTP and helps cancer cells to grow.

KRAS mutations are relatively common oncogenic mutations found in about 20% of solid cancers. In particular, this mutation is most commonly found in adenocarcinomas of the pancreas and colon, lung cancer, and the like. Specifically, when prognosis after treatment of patients with lung cancer, pancreatic cancer, colon cancer, etc. caused by a KRAS mutation is observed, most of the patients have a poorer prognosis than patients without a KRAS mutation. In addition, unlike other non-small cell lung cancers (NSCLCs), all targeted therapies for KRAS mutated cancer have been discontinued in clinical trials due to side effects.

On the other hand, an AAV gene delivery vehicle is safe as a delivery vehicle derived from a non-pathogenic human virus, and has a wide range of hosts without inducing a cellular immune response. In addition, an AAV gene delivery vehicle is able to deliver genes to non-dividing cells and dividing cells, and in particular, expression of a gene delivered by an AAV gene delivery vehicle is characterized by long-term persistence in vivo.

However, due to its inverted terminal repeat (ITR), the AAV has an issue of a poor DNA packaging ability because a protein-coding sequence of up to about 4.4 kb may be encapsidated. In addition, it is preferable that a gene therapy for anticancer treatment is not expressed for a long period of time, but that the introduced gene disappears simultaneously with death of cancer cells.

Therefore, there is a need to develop, as a gene delivery system for anticancer therapy, an AAV complex useful for prevention or treatment of KRAS mutated solid cancers, in which the AAV complex, due to modification of ITR, which is a characteristic of AAVs, has: improved DNA packaging ability; a lowered probability of being inserted into the chromosome of infected cells; improved productivity and expression efficiency; and selectivity in killing KRAS mutated solid cancers.

SUMMARY

In one embodiment, described herein is an adeno-associated virus (AAV) complex, comprising a polynucleotide sequence encoding a runt-related transcription factor 3 (RUNX3) protein between a first inverted terminal repeat (ITR) and a second IRT, wherein in any one of the first ITR and the second ITR, all or part of a stem-loop structure, which is formed of rep-binding element (RBE), RBE', A, A', B, B', C, C', and D regions, is modified. The adeno-associated virus complex may comprise an operably linked SPC promoter, a polynucleotide sequence encoding a RUNX3 protein, and a polyadenylation sequence, between the first ITR and the second ITR. The AAV may be of an AAV serotype selected from the group consisting of AAV1, AAV2, AAV3, AAV4, AAV5, AAV6, AAV7, AAV8, AAV9, AAV10, AAV11, and AAV12. In certain embodiments, the first ITR is not modified and the second ITR is modified. The modification of the stem-loop structure may be insertion, deletion, or substitution. In the complex, any one of the first ITR and the second ITR may be modified to not form a stem-loop structure. In the complex, in any one of the first ITR and the second ITR, all or part of a stem-loop structure, which is formed of rep-binding element (RBE), RBE', A, A', B, B', C, C', and D regions, may be deleted. In wherein any one of the first ITR and the second ITR comprises a terminal resolution site (trs) sequence and an RBE sequence, and has deleted therefrom all of C, C', B', B, RBE', A' and D sequences after RBE. In the complex, the first ITR may be an AAV wild-type ITR, and the second ITR may consist essentially of a nucleotide sequence selected from the group consisting of SEQ ID NOs: 1 to 9. In the complex, the first ITR may be an AAV wild-type ITR, and the second ITR may consist essentially of a nucleotide sequence of SEQ ID NO: 1. The adeno-associated virus complex may further comprise a gene junction comprising SEQ ID NO: 10 between the SPC promoter and the nucleotide sequence encoding RUNX3.

In another embodiment, described herein is a method of treating KRAS mutated lung cancer, comprising administering an effective amount of the adeno-associated virus complex described herein to a subject in need thereof. The lung cancer may be non-small cell lung cancer, or small cell lung cancer, where the non-small cell lung cancer may be selected from the group consisting of squamous cell carcinoma, large cell carcinoma, and lung adenocarcinoma.

In yet another embodiment, described herein is a pharmaceutical composition for preventing or treating KRAS mutated lung cancer, comprising the adeno-associated virus complex described herein. The pharmaceutical composition may further comprise a pharmaceutically acceptable carrier.

BRIEF DESCRIPTION OF THE DRAWINGS

The described embodiments, features, and advantages of certain embodiments of the disclosure will be more apparent from the following description taken in conjunction with the accompanying drawings.

DETAILED DESCRIPTION

Figure 1:
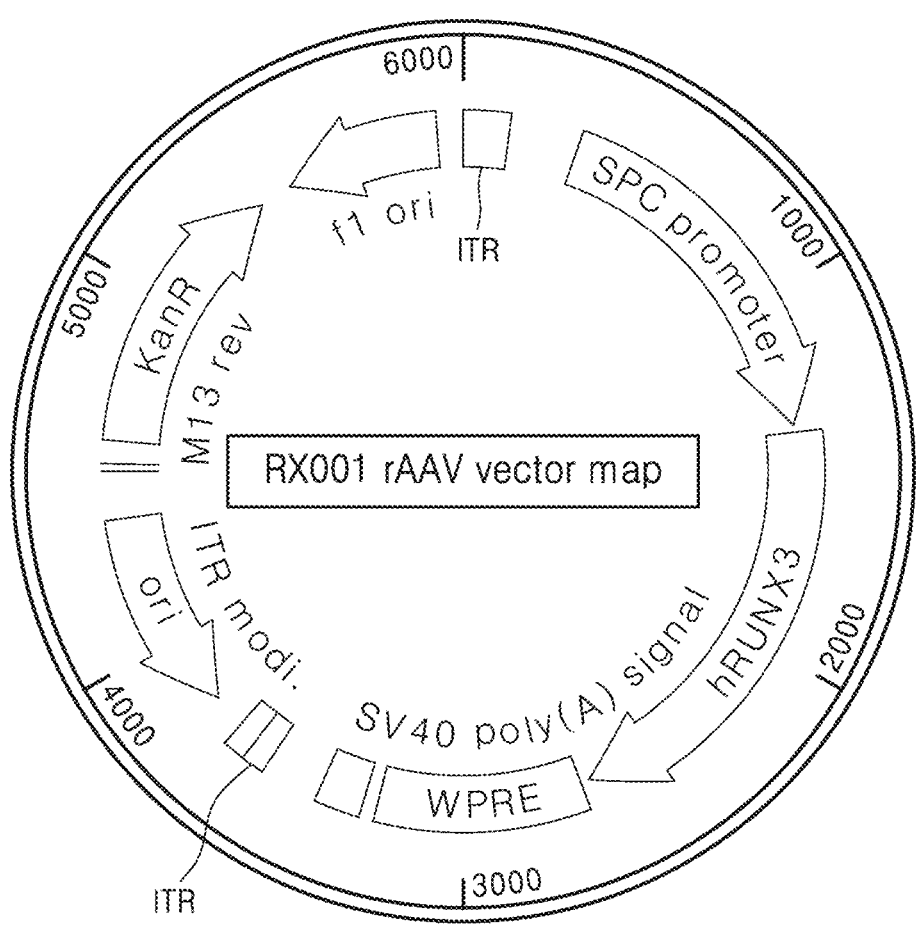
FIG. 1 shows a cleavage map of an adeno-associated virus (AAV) vector according to an example.

Various embodiments will be set forth in part in the description which follows and, in part, will be apparent from the description, or may be learned by practice of the presented embodiments of the disclosure.

In one embodiment, described herein is an adeno-associated virus complex including a modified inverted terminal repeat.

In another embodiment, described herein is a cell transformed by the adeno-associated virus complex.

In yet another embodiment, described herein is a method of treating KRAS mutated cancer including administering an effective amount of the described adeno-associated virus complex.

In yet another embodiment, described herein is a pharmaceutical composition for preventing or treating KRAS mutated lung cancer including the adeno-associated virus complex.

In yet another embodiment described herein is a use of the adeno-associated virus complex for preparation of a therapeutic agent for treating KRAS mutated lung cancer.

In one further embodiment, described herein is an adeno-associated virus (AAV) complex including a modified inverted terminal repeat (ITR).

The term, "adeno-associated virus (AAV)," used herein, refers to a single-chain DNA virus with a genome size of about 4.6 kbp, which is a helper vector-dependent human parvovirus. The genome consists of ITRs at both ends and two open reading frames (ORFs), rep and cap. The N-terminal region of the genome encodes a rep gene involved in viral replication and expression of viral genes, and the C-terminal region encodes a cap gene encoding a viral capsid protein. ITRs are involved in replication of an AAV genome and packaging of AAV particles. ITR includes a rep-binding element (RBE), RBE', A, A', B, B', C, C', and D regions to form a stem-loop structure (hairpin structure). The structure of AAV ITRs is well described, for example in Goncalves, M. A. *Virology Journal*, 2(1):43 (2005), which is incorporated herein by reference.

In certain embodiments, the ITR sequence may be based on an ITR sequence of a virus belonging to the genus *Dependovirus* of the family Parvoviridae.

In certain alternative embodiments, the ITR sequence may be based on an ITR sequence of AAV. The ITR sequence of AAV is publicly known.

AAV includes, e.g., AAV1, AAV2, AAV3, AAV4, AAV5, AAV6, AAV7, AAV8, AAV9, AAV10, AAV11, AAV12, etc., and may also include other AAV serotypes currently known, or to be discovered later. AAV may include known AAV derivatives. AAV may include modified or artificial AAV.

Thus, the ITR sequence may be based on an ITR sequence of an AAV serotype selected from AAV1, AAV2, AAV3, AAV4, AAV5, AAV6, AAV7, AAV8, AAV9, AAV10, AAV11, and AAV12. The ITR sequence may be based on an ITR sequence of an AAV serotype selected from AAV1, AAV2, AAV3, AAV4, AAV5, AAV6, AAV7, AAV8, and AAV9. The first ITR and the second ITR may be based on ITR sequences of the same or different AAV serotypes.

Alternatively, other types of viruses belonging to the genus *Dependovirus* of the family Parvoviridae may be used instead of AAV.

The term "AAV complex," used herein, may be used interchangeably with "AAV vector," "AAV delivery vehicle," "recombinant AAV," and "recombinant AAV vector."

In certain embodiments, the AAV complex includes a polynucleotide sequence encoding a runt-related transcription factor 3 (RUNX3) protein between the first ITR and the second ITR.

The polynucleotide sequence encoding a RUNX3 protein may be operably arranged between the first ITR and the second ITR.

In certain embodiments, the genome of the AAV complex includes a first ITR (5'-ITR), an SPC promoter, a polynucleotide sequence encoding the RUNX3 protein, a polyadenylation sequence, and a second ITR (3'-ITR) in a 5' to 3' direction.

In certain embodiments, the AAV complex includes a polynucleotide sequence encoding a RUNX3 protein between the first ITR and the second ITR, and in any one of the first ITR and the second ITR, all or part of a stem-loop structure, which is formed of RBE, RBE', A, A', B, B', C, C', and D regions, may be modified.

In one embodiment described herein, the AAV complex includes an operably linked surfactant protein C (SPC) promoter, a polynucleotide sequence encoding a RUNX3 protein, and a polyadenylation sequence, between a first ITR and a second ITR.

In certain embodiments, a genome of the AAV complex includes a first ITR (5'-ITR), a SPC promoter, a polynucleotide sequence encoding a RUNX3 protein, a polyadenylation sequence, and a second ITR (3'-ITR), in a 5' to 3' direction.

In certain other embodiments, the AAV complex includes an operably linked SPC promoter, a polynucleotide sequence encoding a RUNX3 protein, and a polyadenylation sequence, between the first ITR and the second ITR, and in any one of the first ITR and the second ITR, all or part of a stem-loop structure, which is formed of RBE, RBE', A, A', B, B', C, C', and D regions, may be modified.

In certain other embodiments, the AAV complex may include an asymmetrically modified ITR. In an embodiment, the AAV complex may have any one of a first ITR and a second ITR modified. In another embodiment, the AAV complex may have a first ITR modified, and a second ITR not modified. In another embodiment, the AAV complex may have a first ITR not modified, and a second ITR modified. In another embodiment, the AAV complex may have 5'-ITR of a (+) strand of a target gene not modified, and 3'-ITR of the (+) strand modified. In another embodiment, the AAV complex may have 5'-ITR of the (−) strand of the target gene modified, and 3'-ITR of the (−) strand not modified. In other words, that the second ITR is modified may mean that the 3'-ITR of the (+) strand and/or the 5'-ITR of the (−) strand of the target gene is modified. An AAV complex according to an aspect may have increased productivity of the AAV complex and an increased expression rate of the RUNX3 gene, by including the asymmetrically modified ITR.

Among the first ITR and the second ITR, the unmodified ITR may be a wild-type ITR. Among the first ITR and the second ITR, the unmodified ITR may be an AAV wild-type ITR.

Among the first ITR and the second ITR, the unmodified ITR may be a functional derivative having substantially the same functional properties with a wild-type ITR (for example, AAV wild-type ITR).

The term "functional derivative," as used herein, may mean a derivative having substantially the same functional properties. The derivative refers to a similar compound obtained by chemically changing a part of a structure of a compound. The derivative may refer to a compound in which a hydrogen atom or a specific atomic group in a compound is substituted with another atom or atomic group. A method of preparing derivatives of a compound while retaining substantially the same functional properties is known in the art.

In any one of the first ITR and the second ITR, all or part of a stem-loop structure, which is formed of rep-binding element (RBE), RBE', A, A', B, B', C, C', and D regions, is modified.

In an embodiment, the modification of the stem-loop structure (hairpin structure) may be selected from insertion, deletion, and substitution.

In an embodiment, the modification of the stem-loop structure (hairpin structure) includes modification to include a single stem and a single loop. For example, the modified ITR may include a deletion of a B-B' arm for a C-C' arm to remain, or a deletion of the C-C' arm for the B-B' arm to remain.

In an embodiment, the modification of the stem-loop structure (hairpin structure) includes modification to include a single stem instead of two loops. For example, a modified ITR may include a deletion of a B-B' arm and a C-C' arm.

In an embodiment, the modified ITR may include a deletion of a C' region for a truncated C-loop and a B-B' arm to remain. Similarly, the modified ITR may include a deletion of a B region for a truncated B-loop and a C-C' arm to remain.

In an embodiment, the modified ITR may include a deletion of a base pair in at least one portion selected from a C portion, a C' portion, a B portion, or a B' portion, such that a single arm may be formed, for complementary base pairings occur between a C portion and a B' portion and between a C' portion and a B portion.

In an embodiment, the modified ITR may include a modification (for example, deletion, substitution, or addition) of 1, 2, 3, 4, 5, or 6 nucleotides in at least one region selected from between A' and C, between C and C', between C' and B, between B and B', and between B' and A.

In an embodiment, the modification of the stem-loop structure (hairpin structure) may include a modification of a structure of a structural element. Specifically, the modification of the structure of a structural element may include an alteration of a height of a stem and/or an alteration of a number of nucleotides in a loop. For example, the height of the stem may be about 2, 3, 4, 5, 6, 7, 8, or 9 nucleotides or more, or any range of nucleotides therein. In another example, the loop may have about 3, 4, 5, 6, 7, 8, 9, 10 nucleotides or more, or any range of nucleotides therein.

In another embodiment, by altering (for example, increasing or decreasing) a distance between two elements (as a non-limiting example, RBE and a hairpin), functional interaction with a large Rep protein may be altered. For example, the distance may be about 1, 2, 3, 4, 5, 6, 7, 8, 9, 10, 11, 12, 13, 14, 15, 16, 17, 18, 19, 20, or 21 nucleotides or more, or any range of nucleotides therein.

In an embodiment, any one of the first ITR and the second ITR may be modified to not form a stem-loop structure (hairpin structure). In another embodiment, the first ITR may be modified to not form a stem-loop structure. In another embodiment, the second ITR may be modified to not form a stem-loop structure. In another embodiment, the first ITR may not be modified, and the second ITR may be modified to not form a stem-loop structure.

The expression "modified to not form a stem-loop sequence (hairpin structure)" may mean that an ITR structure is modified to exist as an open-end or free-end without forming a stem-loop structure (hairpin structure), due to a modification of a ITR sequence. An AAV complex according to an aspect is modified so that any one of the first ITR and the second ITR does not form a stem-loop structure (hairpin structure), to suppress formation of a circular dimer and circular concatemer in infected cells, and to suppress integration into the host genome, which is observed in AAV. In addition, productivity of the AAV complex and a rate of expression of the RUNX3 gene may be increased by the modification.

In an embodiment, any one of the first ITR and the second ITR may be modified to a blunt end. In another embodiment, any one of the first ITR and the second ITR may be modified to a sticky end. In another embodiment, the second ITR may be modified to a blunt end or a sticky end. In another embodiment, the second ITR may be modified to a blunt end. The modification to a blunt end or a sticky end may be performed by using a known method by a person skilled in the art.

In an embodiment, in any one of the first ITR and the second ITR, all or part of a stem-loop structure, which is formed of RBE, RBE', A, A', B, B', C, C', and D regions, may be deleted. In another embodiment, in any one of the first ITR and the second ITR, part of a stem-loop structure, which is formed of RBE, RBE', A, A', B, B', C, C', and D regions, may be deleted. In another embodiment, any one of the first ITR and the second ITR may include a terminal resolution site (trs) sequence and an RBE sequence, and may have deleted therefrom all of C, C', B', B, RBE', A' and D sequences after RBE. In another embodiment, the first ITR may not be modified, and the second ITR may include a trs sequence and an RBE sequence, and may have deleted therefrom all of C, C', B', B, RBE', A' and D sequences after RBE.

In another embodiment, any one of the first ITR and the second ITR may include or consist of any one nucleotide sequence selected from sequences of SEQ ID NOs: 1 to 9, or a complementary sequence thereto. In another embodiment, first ITR may be not modified, and the second ITR may include or consist of any one nucleotide sequence selected from sequences of SEQ ID NOs: 1 to 9, or a complementary sequence thereto.

The sequence of SEQ ID NO: 1 may be based on a sequence of AAV2 ITR.

The sequence of SEQ ID NO: 2 may be based on a sequence of AAV1 ITR.

The sequence of SEQ ID NO: 3 may be based on a sequence of AAV3 ITR.

The sequence of SEQ ID NO: 4 may be based on a sequence of AAV4 ITR.

The sequence of SEQ ID NO: 5 may be based on a sequence of AAV6 ITR.

The sequence of SEQ ID NO: 6 may be based on a sequence of AAV7 ITR.

The sequence of SEQ ID NO: 7 may be based on a sequence of AAV5 ITR.

The sequence of SEQ ID NO: 8 may be based on a sequence of AAV8 ITR.

The sequence of SEQ ID NO: 9 may be based on a sequence of AAV9 ITR.

The sequences of SEQ ID NOs: 1 to 9 may have a portion of an AAV ITR sequence deleted. The sequences of SEQ ID NOs: 1 to 9 may include a trs sequence and a RBE sequence among AAV ITR sequences. The sequences of SEQ ID NOs: 1 to 9 may have deleted therefrom all of C, C', B', B, RBE', A' and D sequences after RBE.

In general, an RNA polymerase generates mRNA having a sequence complementary to a target gene in a promoter region. The process is called "transcription" and the transcription is proceeded in a 5' to 3' direction. Meanwhile, when a target gene is inserted into the AAV complex, the gene is inserted in the 5' to 3' direction and a 3' to 5' direction, respectively, with respect to the double helix of DNA of the AAV complex. Therefore, while the transcription of the target gene is in progress, transcription of the target gene occurs in both directions due to the double helix of DNA of the AAV complex, and thus, there is an issue that an expression efficiency of the target gene is lowered due to interference. However, an AAV complex according to an aspect may enhance expression efficiency of a target gene by avoiding interference by the double helix structure of DNA of the AAV complex during transcription of a target gene, by a modification of the stem-loop structure, specifically, by a deletion of all or part of the stem-loop structure.

For example, in an AAV complex including an asymmetrically modified ITR, a first ITR may not be modified, and a second ITR may be modified to not form a stem-loop structure. Accordingly, 5'-ITR of the (−) strand of the RUNX3 gene does not form a hairpin structure, and transcription of the RUNX3 gene proceeds complementary to the corresponding strand in the 5' to 3' direction. Meanwhile, in the (+) strand of the RUNX3 gene, 3'-ITR does not form a hairpin structure, and transcription of the RUNX3 gene does not proceed in the corresponding strand. That is, since only the 5' to 3' direction transcription of the delivered gene proceeds, and a competitor in the 3' to 5' direction is removed, gene expression efficiency may be increased.

In an example, in an AAV vector including an RUNX3 gene, an AAV complex (Example 1) including an asymmetrically modified ITR was prepared by partially modifying a hairpin structure of a second ITR among AAV wild-type ITRs included in the vector. The prepared AAV complex was compared with an AAV complex (Comparative Example 1), in which the hairpin structure is not modified, and with an AAV complex (Comparative Example 2) modified so that both ends of the hairpin structure are symmetrical, and productivity and an RUNX3 gene expression rate of each AAV complex were confirmed. As a result, it was confirmed that the AAV complex (Example 1) including the asymmetrically modified ITR has viral productivity increased by 3 times or more, and an RUNX3 gene expression rate increased by 6 times or more, compared to the AAV complex without ITR modification (Comparative Example 1) and the AAV complex containing the symmetrically modified ITR (Comparative Example 2).

The term, "runt-related transcription factor 3 (RUNX3) protein," used herein, refers to a protein expressed by a RUNX3 gene, and is a member of the RUNX family consisting of RUNX1, RUNX2, and RUNX3. Genes belonging to the RUNX family play an important role in normal development and tumorigenesis, and function as transcription regulatory factors of TGF-β and the Smad family, a subfactor that mediates signal transduction of TGF-β.

The RUNX3 protein may include at least one amino acid sequence selected from SEQ ID NO: 19 and SEQ ID NO: 20. In addition, a polynucleotide sequence encoding the RUNX3 protein may be selected from SEQ ID NOS: 21 and 22.

The RUNX3 protein may be derived from a human or an animal.

The RUNX3 protein may be synthesized by a chemical synthesis method (W. H. Freeman and Co., Proteins; structures and molecular principles, 1983) in the art, and may be prepared by a genetic engineering method (Maniatis et al., Molecular Cloning: A laboratory Manual, Cold Spring Harbor laboratory, 1982; Sambrook et al., Molecular Cloning: A Laboratory Manual; etc.) in the art.

The RUNX3 protein may be a variant of amino acids having a different sequence by deletion, insertion, substitution, or a combination thereof of amino acid residues, within a range that does not affect a function of the protein. Amino acid exchanges in proteins that do not entirely alter activity of the molecules are known in the art. In some cases, the amino acids may be modified by phosphorylation, sulfation, acrylation, glycosylation, methylation, farnesylation, or the like.

Therefore, in an embodiment, the RUNX protein may include a peptide and a variant or a fragment thereof, the peptide having an amino acid sequence substantially identical to a protein including any one or more amino acid sequences selected from SEQ ID NOS: 19 and 20. The substantially identical protein may have homology of 80% or more, specifically 90% or more, or more specifically 95% or more, with the RUNX3 protein.

In an embodiment, the AAV complex may further include post-transcriptional regulatory elements. The AAV complex may include a first ITR, a SPC promoter sequence, a polynucleotide sequence encoding a RUNX3 protein, post-transcriptional regulatory elements, a polyadenylation sequence, and a second ITR, in the 5' to 3' direction.

The post-transcriptional regulatory element may include a woodchuck hepatitis virus post-transcriptional regulatory element (WPRE).

In an embodiment, the AAV complex may further include a gene junction between the SPC promoter and the polynucleotide sequence encoding the RUNX3 protein.

The term "gene junction", used herein, refers to a sequence that is not defined and is located between the end of a promoter and the start of a target gene sequence. Specifically, a promoter is a site where transcription machinery is complexly bound to regulate genes, and a boundary, between the end of a known promoter sequence and the start region of a gene whose expression is to be controlled, is generally ambiguous. Thus, optimization of the junction may be needed to construct a successful promoter-gene expression relationship.

Accordingly, in order to regulate expression of the RUNX3 gene by an SPC promoter, the present inventors found optimized sequences by substituting with various combinations of polynucleotides, and confirmed that a polynucleotide in a range of 22 bp to 28 bp was suitable. Among the optimized sequences, since promoter DNA and RUNX3 DNA sequences may be prepared by PCR by using primers designed to have restriction enzymes that are not included in the vector body or the DNA sequence to be amplified, junctions, which have an additional site for a restriction enzyme that does not cleave the vector, promoter, or gene sequences, were finally selected.

Thus, in an embodiment, the gene junction may include SEQ ID NO: 11. In addition, the gene junction may determine whether or not to express the RUNX3 gene or affect expression efficiency of the RUNX3 gene, depending on its length or structure.

The AAV complex may be engineered to encode selectable markers or reporters that provide means for selection or identification of cells that have incorporated them. Selectable markers or reporters are known in the art. Non-limiting examples of the selectable markers include genes conferring resistance to ampicillin, streptavidin, kanamycin, hygromycin, and the like. Non-limiting examples of the reporters include luciferase, green fluorescent protein (GFP), and the like.

Another aspect provides a cell transformed by an adeno-associated virus complex according to an aspect.

Details of the adeno-associated virus complex are as described above.

The term "transformation," used herein, means that genetic properties of an organism are changed by DNA introduced from outside. Transformation is a phenomenon in which DNA enters a cell and changes hereditary traits, when DNA, a type of nucleic acid extracted from a cell line of an organism, is injected into a living cell of another cell line. That is, "transformation" means introducing a gene into a host cell so that it may be expressed in the host cell.

In certain embodiments, a method of transforming a cell line by introducing an AAV complex may be a method known in the art, for example, transient transfection by using lipofectamine, etc. microinjection, transduction, cell fusion, calcium phosphate precipitation, liposome-mediated transfection, DEAE dextran-mediated transfection, polybrene-mediated transfection, electroporation, etc., but is not limited thereto, and preferably, lipofectamine 2000 reagent may be used for transformation.

Another aspect provides a method of preventing or treating lung cancer including administering an effective amount of the adeno-associated virus complex according to an aspect to a cell or subject.

Details of the adeno-associated virus complex are as described above.

In the method described herein, the AAV complex may be administered to a subject by itself, or the AAV complex may be formulated into a form administrable to a subject and administered to the subject. In an embodiment, the AAV complex may be administered to a subject in a form of a composition including an AAV complex according to the following aspect. For example, the AAV complex may be formulated into a composition including the AAV complex and a pharmaceutically acceptable carrier, and administered to a subject.

The subject may be one in need of expression of a RUNX3 gene delivered by the AAV complex. The subject may be one suffering from or highly likely to suffer from a disease to which gene therapy is applicable. The subject may be one suffering from or highly likely to suffer from a disease that may be treated by expression of a RUNX3 gene delivered by an AAV complex. The subject may be a mammal, such as a human, a cow, a horse, a pig, a dog, sheep, a goat, or a cat. The subject may be a subject suffering from or is highly likely to suffer from cancer.

The lung cancer may be KRAS mutated lung cancer.

The term "KRAS mutated lung cancer," used herein, refers to lung cancer in which a KRAS mutated gene is activated and cancer suppressor genes are inactivated. When activity of the cancer suppressor gene is restored, as lung cancer cells are removed and normal cells remains, KRAS mutated lung cancer can be treated. The cancer suppressor gene may be, for example, sPD-1, VHL, MMAC1, DCC, p53, NF1, WT1, Rb, BRAC1, BRAC2, or RUNX3 genes.

In an embodiment, the lung cancer may be non-small cell lung cancer, or small cell lung cancer. The non-small cell lung cancer includes, for example, squamous cell carcinoma, large cell carcinoma, lung adenocarcinoma, and the like.

In an example, it was confirmed that when a recombinant AAV including a RUNX3 gene was injected into non-small cell lung cancer mouse models in which the KRAS mutation was activated, death of the lung cancer cells was promoted, and cancer development was inhibited. In addition, as a result of infecting a normal lung epithelial cell line and a non-small cell lung cancer cell line, it was confirmed that RUNX3 and cell death markers were significantly increased in the lung cancer cell line, whereas there was no change in a cell death rate in the normal lung epithelial cells.

Therefore, an AAV complex according to an aspect may specifically remove lung cancer cells by activating the RUNX3 gene in lung cancer caused by decreased activity of RUNX3 proteins, and thus, may be used to prevent or treat KRAS mutated lung cancer. In addition, recurrence of the KRAS mutated lung cancer may be prevented.

The term, "prevention," used herein, refers to all actions that suppress or delay an onset of a disease by administration of the AAV complex. The term "treatment" refers to all actions that ameliorate or beneficially alter symptoms of a disease by administration of the AAV complex.

In certain embodiments, the method may further include administering a second active ingredient to the subject. The second active ingredient may be an active ingredient for preventing or treating lung cancer. The active ingredient may be administered concurrently, separately, or sequentially with the AAV complex.

The AAV complex may be formulated into an injectable formulation suitable for administration by any suitable route, such as intravenous, intraarterial, subcutaneous, intradermal, intraperitoneal, intramuscular, intraarticular, or intrathecal, and may be administered to a subject. The AAV complex may be administered systemically or locally, and may be administered alone or in combination with other pharmaceutically active compounds.

A preferable dosage of the AAV complex may vary depending upon the patient's condition and body weight, severity of the disease, formulation of the therapeutic agent, route and duration of administration, etc., and may be appropriately selected by those skilled in the art. In an embodiment, a dosage of the AAV complex may be about $1.0 \times 10^6$ vg/kg to about $1.0 \times 10^{16}$ vg/kg, about $1.0 \times 10^1$ vg/kg to about $1.0 \times 10^{16}$ vg/kg, about $1.0 \times 10^{10}$ vg/kg to about $1.0 \times 10^{16}$ vg/kg, about $1.0 \times 10^1$ vg/kg to about $1.0 \times 10^1$ vg/kg, about $1.0 \times 10^{12}$ vg/kg to about $1.0 \times 10^{14}$ vg/kg, for example, about $1.0 \times 10^{12}$ vg/kg, about $1.0 \times 10^{13}$ vg/kg, or about $1.0 \times 10^{14}$ vg/kg. In a certain embodiment, a dosage of the AAV complex may be about $1.0 \times 10^{13}$ vg/kg. The administration may be performed once a day, multiple times a day, once a week, once every 2 weeks, once every 3 weeks, or once every 4 weeks to once a year.

The term "about," used herein, is used to include a range of ±10% of a designated numerical value.

Another aspect provides a pharmaceutical composition for preventing or treating lung cancer including an adeno-associated virus complex according to an aspect. Still another aspect provides a use of an adeno-associated virus complex according to an aspect, for preparation of a therapeutic agent for lung cancer.

Details of the adeno-associated virus complex and lung cancer are as described above.

The pharmaceutical composition may include a pharmaceutically acceptable carrier. The carrier includes an excipient, diluent, or auxiliary agent. As the carrier, a carrier suitable for delivering the AAV complex into a living body may be used. Specifically, for the carrier, a carrier suitable for formulation into a parenteral formulation (for example, an injection formulation) may be selected. For example, for the carrier, a carrier suitable for formulation into an intravenous formulation may be selected. The carrier may be an aqueous solution, such as water or buffered saline solution and the like.

The pharmaceutical composition may be prepared in any formulation according to a method in the art. The composition may be formulated in a form suitable for delivery of an AAV vector to a subject. The composition may be formulated in an aqueous solution, for example, in water or a buffered saline solution. The composition may be formulated, for example, as a parenteral formulation (for example, as an injection, for example, for bolus injection, or continuous infusion). In an embodiment, the pharmaceutical composition may be formulated as an injectable formulation suitable for administration via any suitable route, such as intravenous, intraarterial, subcutaneous, intradermal, intraperitoneal, intramuscular, intraarticular, or intrathecal. In a certain embodiment, the composition may be formulated to be administered via intravenous injection, or subcutaneous injection. In addition, the composition may be prepared as a systemic formulation, or topical formulation. The composition may be provided as ampoules, prefilled syringes, small injection containers, or a unit dosage form in multi-dose containers with added preservatives.

In certain embodiments, the pharmaceutical composition may further include one or more anticancer agent(s). Exemplary anticancer agents include cetuximab, panitumumab, erlotinib, gefitinib, trastuzumab, T-DM1, perjeta, lapatinib, paclitaxel, taxol, tamoxifen, cisplatin, or combinations thereof. The pharmaceutical composition may be a single composition, or separate compositions. For example, the composition of antibodies or antigen-binding fragments thereof may be a composition of a parenteral dosage form, and the anticancer agent may be a composition of an oral dosage form.

The pharmaceutical composition may contain an effective amount of the AAV complex. The term "effective amount" refers to an amount that is sufficient to lead to a desired preventive or therapeutic effect when administered to a subject in need thereof. The effective amount may be selected by those skilled in the art depending on the cell or the subject. The effective amount may be determined according to severity of the disease, an age, weight, health, sex, and sensitivity to a therapeutic agent of a patient, time of administration, a route of administration, an excretion rate, duration of treatment, factors including therapeutic agents used in combination with or concurrently with the composition used, and other factors well-known in the medical field.

In an embodiment, the pharmaceutical composition may include the AAV complex in a dosage of about $1.0 \times 10^6$ vg/kg to about $1.0 \times 10^{16}$ vg/kg, about $1.0 \times 10^8$ vg/kg to about $1.0 \times 10^{16}$ vg/kg, about $1.0 \times 10^{10}$ vg/kg to about $1.0 \times 10^{16}$ vg/kg, about $1.0 \times 10^{10}$ vg/kg to about $1.0 \times 10^{14}$ vg/kg, about $1.0 \times 10^{12}$ vg/kg to about $1.0 \times 10^{14}$ vg/kg, for example, about $1.0 \times 10^{12}$ vg/kg, about $1.0 \times 10^3$ vg/kg, or about $1.0 \times 10^{14}$ vg/kg. In a certain embodiment, the pharmaceutical composition may include AAV complex of a dosage of about $1.0 \times 10^{13}$ vg/kg. The administration may be performed once a day, multiple times a day, once a week, once every 2 weeks, once every 3 weeks, or once every 4 weeks to once a year.

Reference will now be made in detail to embodiments, embodiments of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of at least one of the associated listed items. Expressions such as "at least one of," when preceding a list of elements, modify the entire list of elements and do not modify the individual elements of the list.

Hereinafter, preferred examples are presented to aid understanding of the present disclosure. However, the following examples are only provided for more easier understanding the present disclosure, and the content of the present disclosure is not limited by the following examples.

EXAMPLES

Example 1. Preparation of Adeno-Associated Virus Complex Including Asymmetrically Modified ITR, for Expression of RUNX3 Gene 1-1. Preparation of Adeno-Associated Virus Vector Introduced with RUNX3 Gene and SPC Promoter Adeno-associated virus (AAV) vectors introduced with a RUNX3 gene were prepared. Specifically, after synthesizing human RUNX3 gene (NCBI reference: NM_004350.2, 412 nt to 1659 nt), PCR amplification was performed by using primers shown in Table 1 below. In this regard, the primers were prepared by synthesizing restriction enzymes Kpnl and Hindlll. In addition, a surfactant protein C (SPC) promoter (GenBank accession no. AC122268, 148366 nt to149406 nt) specifically expressed in lung epithelial cells was PCR amplified by using the primers shown in Table 1 below. In this regard, the primers were prepared by synthesizing restriction enzymes Nhel and Kpnl. Thereafter, each of the amplified RUNX3 and SPC promoter DNA was treated with restriction enzyme Kpnl, and then Kpnl sites were ligated by using T4 DNA ligases to prepare Nhel-SPC-Kpnl-RUNX3-Hindlll DNA strands. Then, an Nhel-SPC-Kpnl-RUNX3-Hindlll DNA strand was cloned while removing a GFP gene present on an Nhe-Hindlll site of a multi cloning site (MCS) of adeno-associated virus (AAV) 2 GFP-vectors (Chungbuk National University Tumor Research Institute). To induce expression of the SPC promoter in the AAV2-GFP vectors, chicken beta actin promoters were removed by using restriction enzymes Ndel and Bglll. Then, in AAV2-SPC-RUNX3 plasmids from which the chicken beta actin promoters were removed, ampicillin resistance genes were removed by using BspHI restriction enzyme sites present at both ends of the ampicillin resistance genes. A kanamycin resistance gene was inserted at a site from which the ampicillin resistance gene was removed. In this regard, the kanamycin resistance gene was recombined by using PCR primers in Table 1 below.

TABLE 1

| Gene | SEQ ID NO: | Direction | Sequence |
|---|---|---|---|
| RUNX3 | 11 | Forward | 5'-tggtaccgcggccaccatgcgtattcccgtaga-3' |
|  | 12 | Reverse | 5'-aagctttactcgagtcagtagggccgccaca-3' |
| SPC | 13 | Forward | 5'-ctgctagcagaaggcagc-3' |
|  | 14 | Reverse | 5'-ggtaccactagtgatatcttttgtaaggtttc-3' |
| Kanamycin | 15 | Forward | 5'-TGTATCCGCTCATGAGAGCTCGGTCATAGCTGTTTCCTG-3' |
|  | 16 | Reverse | 5'-GGATTTTGGTCATGAGCATGCTTAGAAAAACTCATCGAGC-3' |

1-2. Modification of ITR Structure

Site directed mutagenesis was induced, in order to modify a part of a hairpin structure of a second ITR among AAV2 wild-type inverted terminal repeats (ITRs) included in the vectors prepared in Example 1-1. Specifically, among the AAV2 wild-type ITRs included in the vector, from a rep-binding element (RBE) of the 5'-direction ITR of a (−) strand of the RUNX3 gene, all or at least one of C, C', B', B, RBE', A' and D sequences was deleted by using 5'-phosphorylated primers of Table 2 below. For example, all of C, C', B', B, RBE', A' and D sequences were deleted, from RBE of the 5'-direction ITR of the (−) strand of the RUNX3 gene. Accordingly, the second ITR was modified so as not to form a hairpin structure. As a result, an adeno-associated virus complex for expression of the RUNX3 gene including an asymmetrically modified ITR, in which a first ITR was not modified and the second ITR was modified, was obtained.

FIG. 1 shows a cleavage map of an adeno-associated virus vector according to an example.

Figure 2:
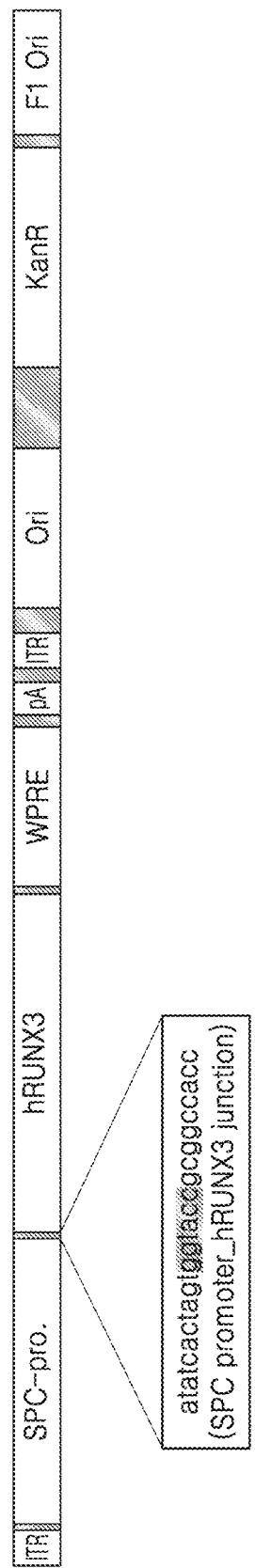
FIG. 2 shows a structure of an AAV vector according to an example.

FIG. 2 shows a structure of an adeno-associated virus vector according to an example.

Figure 3A:
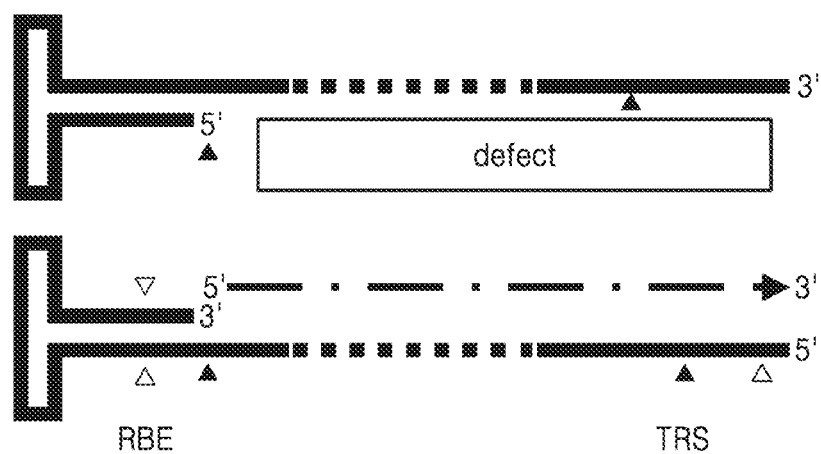
FIG. 3A is a schematic diagram of a genome of an AAV vector including an asymmetrically modified ITR of Example 1.

FIG. 3A is a schematic diagram of a genome of an adeno-associated virus vector including an asymmetrically modified ITR of Example 1.

TABLE 2

| Name | SEQ ID NO: | Direction | Sequence |
|---|---|---|---|
| 5'-Phosphorylation | 17 | Forward | 5'-P-cactgactcgctgcgctcggtcgtt-3' |
|  | 18 | Reverse | 5'-P-agcgagtcagtgagcgagcgagcgc-3' |

Comparative Example

Comparative Example 1. Preparation of AAV Complex Including Symmetrically Unmodified ITR, for Expression of RUNX3 Gene An AAV complex including an unmodified symmetrical ITR was prepared in the same manner as in Example 1-1, except that the ITR hairpin structure was not modified.

Figure 3B:
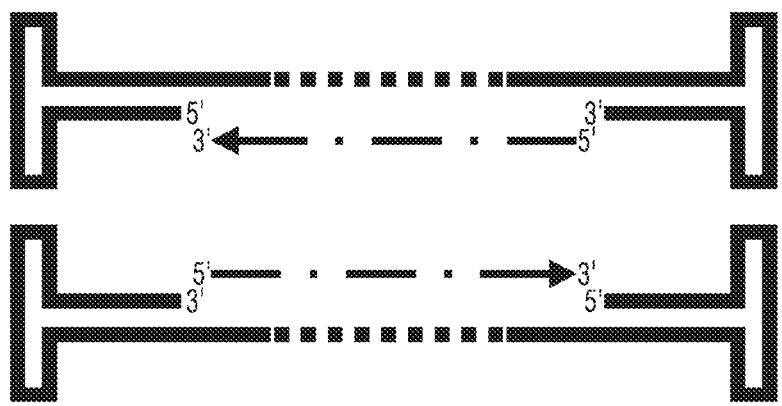
FIG. 3B is a schematic diagram of a genome of an AAV vector including an unmodified symmetrical ITR of Comparative Example 1.

FIG. 3B is a schematic diagram of a genome of an AAV vector including unmodified symmetrical ITR of Comparative Example 1.

Comparative Example 2. Preparation of AAV Complex Including Symmetrically Modified ITR, for Expression of RUNX3 Gene An AAV complex including an ITR modified in order that both ends are symmetrical to each other was prepared in the same manner as in Example 1-2, except that a C-C'-B'-RBE sequence was deleted from both ends of ITR of the AAV complex prepared in Example 1-1.

Figure 3C:
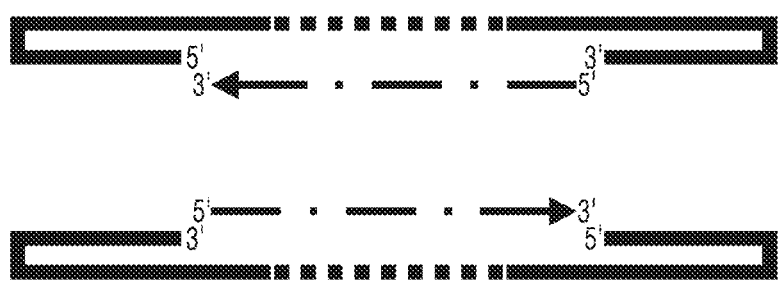
FIG. 3C is a schematic diagram of a genome of an AAV vector including a symmetrically modified ITR of Comparative Example 2.

FIG. 3C is a schematic diagram of a genome of an AAV vector including a symmetrically modified ITR of Comparative Example 2.

Experimental Examples

Experimental Example 1. Confirmation of Productivity of AAV Complex

Productivity of recombinant AAV complexes according to an aspect was confirmed. Specifically, the AAV complexes prepared in Example 1 and Comparative Examples 1 and 2 were transformed into 293T cells, which are human embryonic kidney (HEK) cells, and numbers of virus particles expressed in the cells were measured. As a negative control group, a wild-type AAV complex was used.

First, 293T cells (Chungbuk National University Tumor Research Center) cultured in Dulbecco's modified eagle medium (DMEM, Welgene, LM001-05) supplemented with 10% fetal bovine serum (Weigene, S001-01) and 1×antibiotic (Welgene, LS203-01) were divided into $1\times10^6$ in 75 T flasks (SPL, 70075) and cultured for 24 hours. Then, for transformation, the virus complexes prepared in Example 1 and Comparative Examples 1 and 2, helper plasmids (aldevron) and AAV2 rep/cap plasmids (aldevron) were mixed at 1:3:1 (9 µg: 27 µg: 9 µg) to prepare a mixture. Then, 100 µl of TOMTMT (Welgene, TR 004-01) was added, and after adding Transfection Grade Linear Polyethylenimine Hydrochloride (PEI, MW 40,000) (Polysciences Inc, 24765-1) at a ratio of 1:2 (45 µl: 90 µl) with respect to a total amount of the plasmids, the mixture was left at room temperature for 15 minutes. After refreshing the cell culture medium, the above mixture was added, and after 48 hours or 72 hours, 0.5 M of EDTA, pH 8.0 (TransLab, 15-10ED18), corresponding to 1/80 of the total volume, was added and left for 10 minutes at room temperature for the cells to float. The suspended cells were collected in a 50 ml centrifuge tube (SPL, 50050), a first centrifugation was performed for 10 minutes at 2,000 g and 4° C., and then a second centrifugation was performed for 1 minute under the same conditions to completely remove the supernatant. Then, viral DNA was extracted by using RT-PCR, and the extracted DNA was quantified by using qPCR. Table 3 shows numbers of virus particles expressed in 293T cells.

TABLE 3

| Virus | Productivity (particle number/ml) |
| --- | --- |
| Negative control group | $2.2 \times 10^9$ |
| Example 1 | $9.6 \times 10^9$ |
| Comparative Example 1 | $3.3 \times 10^9$ |
| Comparative Example 2 | $2.3 \times 10^9$ |

As a result, as shown in Table 3, Example 1 was confirmed to have a markedly high number of AAV complex particles than that of the negative control group and Comparative Examples 1 and 2. Specifically, the number of particles in Example 1 was about 4 times higher than that of the negative control group and Comparative Example 2, and about 3 times higher than that of Comparative Example 1.

That is, productivity of the AAV complex according to an aspect may be improved by asymmetric modification of ITR.

Experimental Example 2. Confirmation of Gene Expression Rate of AAV Complex

A target gene expression rate of a recombinant AAV complex according to an aspect was confirmed. Specifically, H460, a non-small cell lung cancer cell line, was infected with the same amount of the complexes prepared in Example 1 and Comparative Examples 1 and 2. After 48 hours, the cells were disrupted to purify the protein, loaded on an SDS page gel, and expression rates of the RUNX3 gene were confirmed by Western blotting. Then, gene expression rates of Example 1 and Comparative Examples 1 and 2 were calculated by setting a degree of detection of the purified RUNX3 proteins as 100%. As a negative control group, a wild-type AAV complex was used. In addition, as an additional negative control, a HEK293 cell line not infected with an AAV complex was used. Unlike cancer cells that do not express RUNX3 well, since HEK293 cells are normal cells, not cancer cells, a large amount of endogenous RUNX3 gene expression was detected.

Figure 4A:
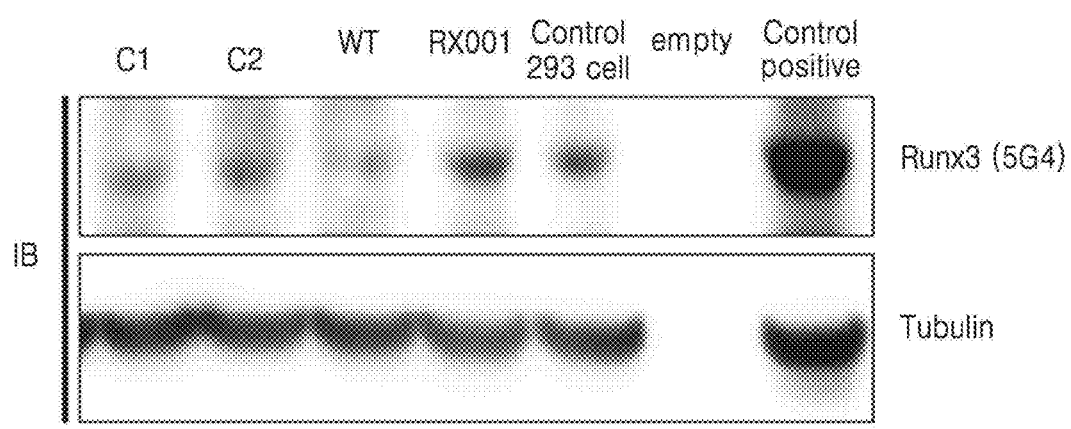
FIG. 4A shows results of confirming, by Western blot, the expression of a target gene in an AAV complex according to an aspect. C1: AAV complex of Comparative Example 1, C2: AAV complex of Comparative Example 2, WT: wild-type AAV complex, RX001: AAV complex of Example 1, Control 293 cell: HEK293 cell line not infected with AAV complex, empty: culture medium with nothing added (double negative control), Control positive: purified RUNX3 protein.

FIG. 4A shows results of confirming expression of a target gene in an AAV complex according to an aspect with Western blot.

Figure 4B:
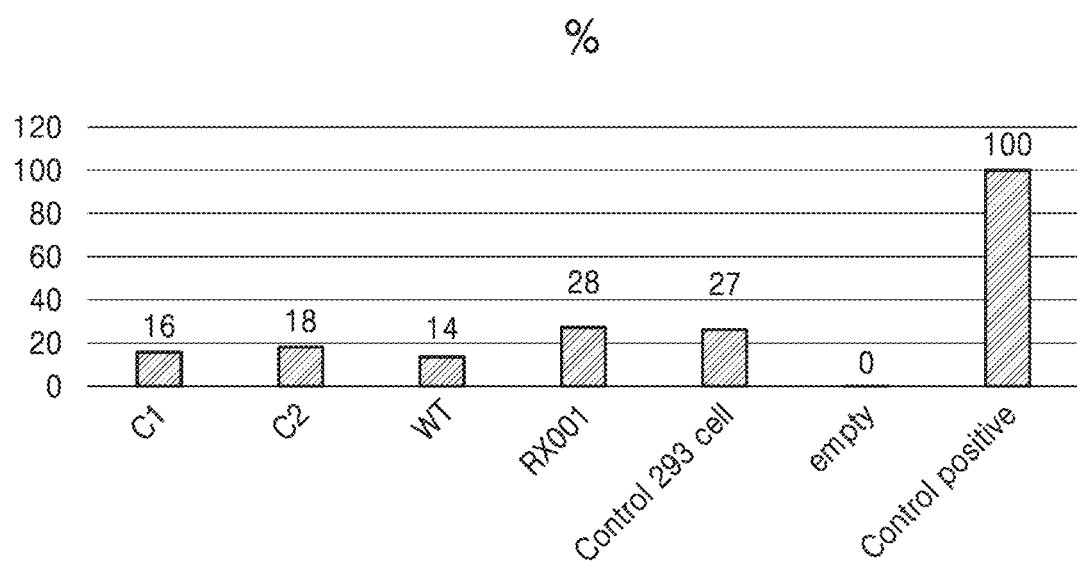
FIG. 4B shows results of quantifying an expression rate of a target gene in an AAV complex according to an aspect, C1: AAV complex of Comparative Example 1, C2: AAV complex of Comparative Example 2, WT: wild-type AAV complex, RX001: AAV complex of Example 1, Control 293 cell: HEK293 cell line not infected with AAV complex, empty: culture medium with nothing added (double negative control), Control positive: purified RUNX3 protein.

FIG. 4B shows results of quantifying an expression rate of a target gene in an AAV complex according to an aspect.

As a result, as shown in FIGS. 4A and 4B, it was confirmed that an expression rate of the RUNX3 gene in the virus produced in Example 1 was significantly increased by more than two times compared to the negative control group and Comparative Examples 1 and 2.

Taken together with the results of Experimental Example 1, the AAV complex according to an aspect had productivity increased by 3 times or more, and an expression rate of the RUNX3 gene increased by more than 2 times, and as a result, it may be seen that efficiency was increased by about 6 times or more.

Experimental Example 3. Confirmation of Lung Cancer Treatment Effect of AAV Complex

3-1. Confirmation of Cell Death in KRAS Mutated Non-Small Cell Lung Cancer

An effect of inducing cell death of the recombinant AAV complex according to an aspect on KRAS mutated non-small cell lung cancer was confirmed. Specifically, C57B6 mice (6 weeks to 8 weeks old) having a genotype of Runx3$^{lox/lox}$;KRAS$^{wt/LSL}$ were infected with adeno5-CRE $2.5\times10^{e7}$ particles, an inducer capable of depleting RUNX3 while activating KRAS mutations, through the respiratory tract. Thereafter, after breeding the mice for 6 weeks to determine whether or not they developed non-small cell lung cancer, the AAV complexes of Example 1 or Comparative Example 1 were infected through the respiratory tract of mice confirmed to develop lung cancer. After 2 weeks, the mice were euthanized, and the lung tissues were extracted to prepare specimens for histopathological examination. Thereafter, the specimens were stained with hematoxylin & eosin (H&E) and terminal deoxynucleotidyl transferase dUTP nick-end labeling (TUNEL), and the stained tissues were observed under a microscope.

Figure 5A:
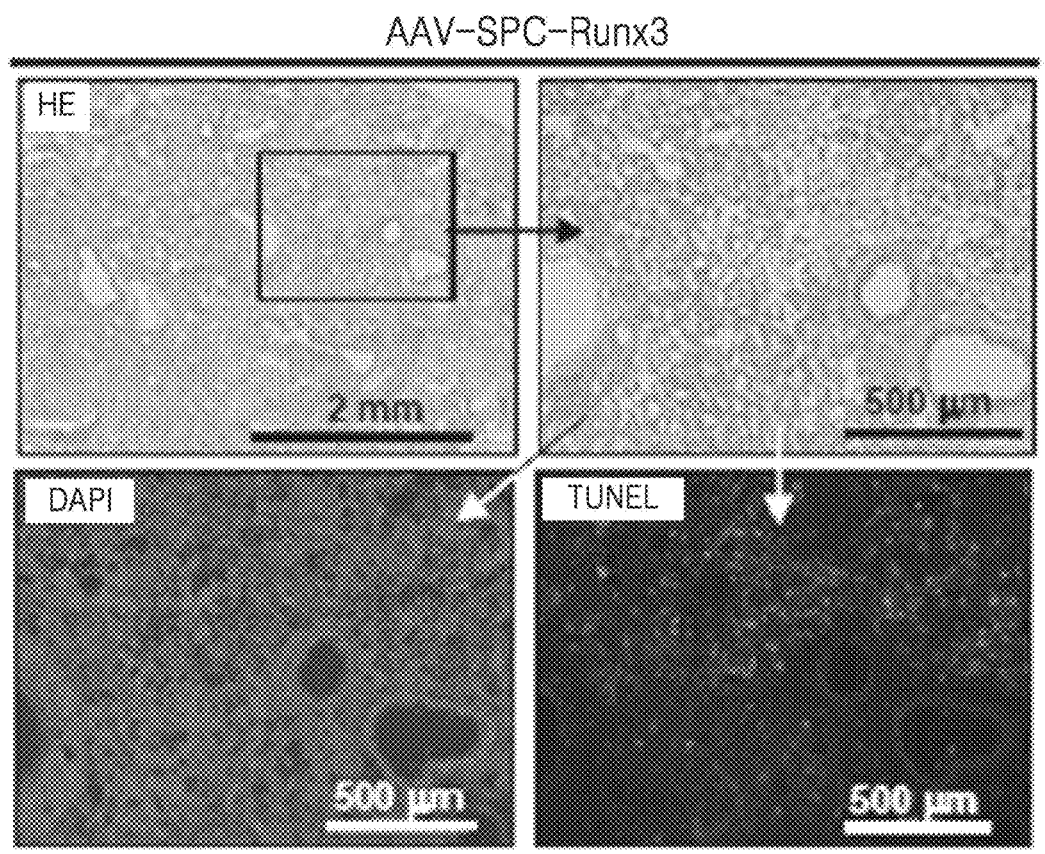
FIGS. 5A and 5B show results of H&E and TUNEL staining of lung cancer tissues infected by Example 1 and Comparative Example 1, respectively.
Figure 5B:
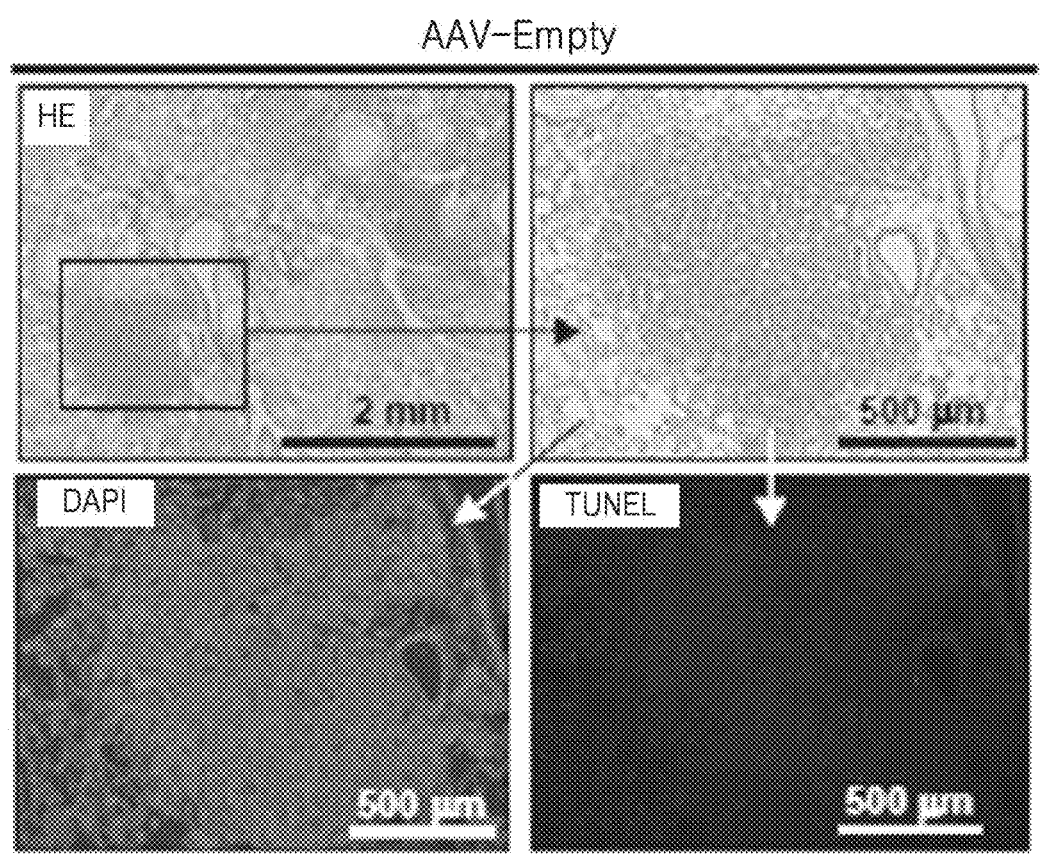

FIGS. 5A and 5B show results of H&E and TUNEL staining of lung cancer tissues infected with Example 1 and Comparative Example 1, respectively.

As a result, as shown in FIG. 5A, for a lung cancer tissue infected with the AAV complex of Example 1, a high level of TUNEL staining was observed in cancerous regions, and it was confirmed that intervals between H&E-stained regions were relatively wide. On the other hand, as shown in FIG. 5B, for a lung cancer tissue infected with the AAV complex of Comparative Example 1, a TUNEL staining was rarely observed, and it was confirmed that intervals between H&E-stained regions were relatively narrow.

That is, it may be seen that in the lung cancer tissue infected by Example 1, cell death occurred at the cancerous site, and no cancer mass was observed, and an original lung structure was maintained. Therefore, the AAV complex according to an aspect promotes death of lung cancer cells and suppresses occurrence of cancer, and thus may be useful for preventing or treating lung cancer.

3-2. Confirmation of Cell Death in Human Non-Small Cell Lung Cancer

An effect of inducing cell death of the recombinant AAV complex according to an aspect on non-small cell lung cancer was confirmed. Specifically, non-small cell lung cancer cell lines H460 and Calu6 and a normal lung cell line WI38 were infected with the AAV complex of Example 1. Thereafter, each of the cell lines was cultured for 1 day to 7 days, and whether cell death occurred was confirmed by flow cytometry (fluorescence-activated cell sorting; FACS) every 1 day to 3 days from day 0 of culturing for 3 days to 7 days. In addition, after extracting proteins from the H460 cell line, expression of RUNX3 and cleaved caspase 3 was confirmed by Western blotting.

Figure 6A:
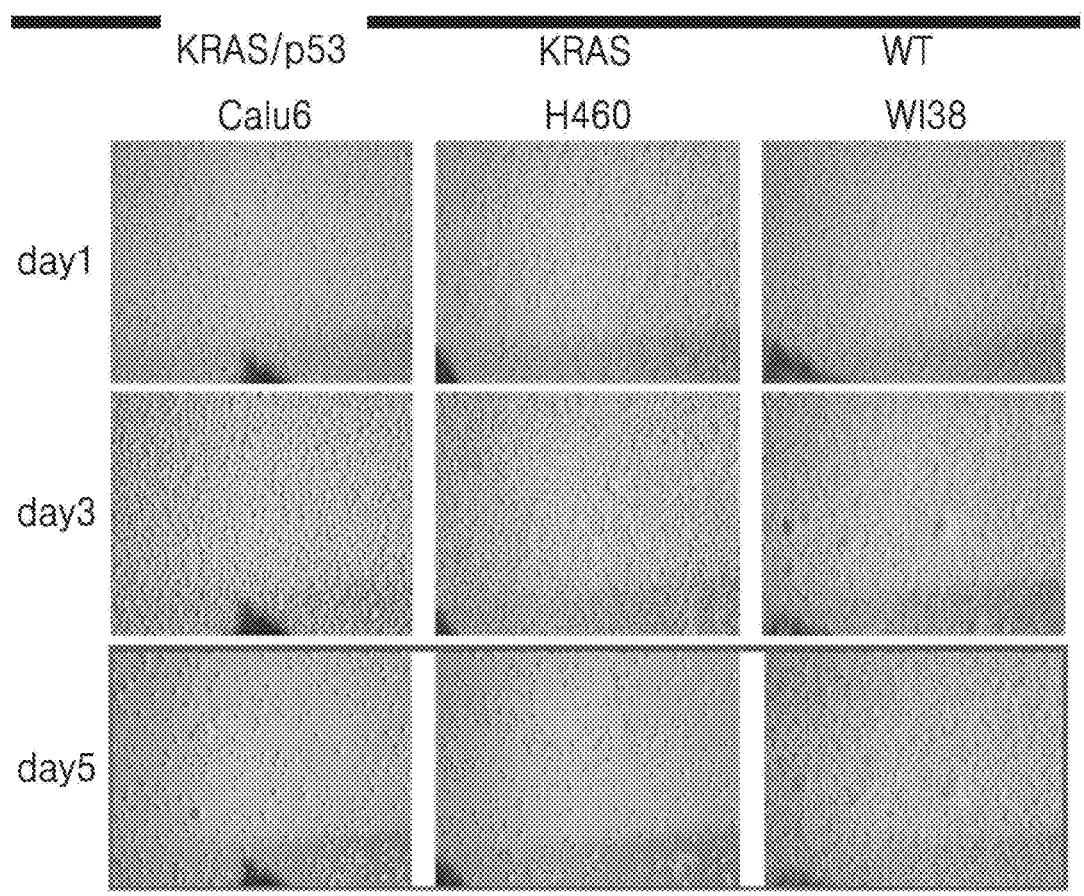
FIG. 6A shows photos taken with a microscope at 1 day, 3 days, and 5 days after infecting KRAS mutated lung cancer cell lines (H460, Calu6) and normal lung epithelial cells (WI38) with Example 1.

FIG. 6A shows micrographs taken 1 day, 3 days, and 5 days after infecting KRAS mutated lung cancer cell lines (H460, Calu6) and normal lung epithelial cells (WI38) with Example 1.

Figure 6B:
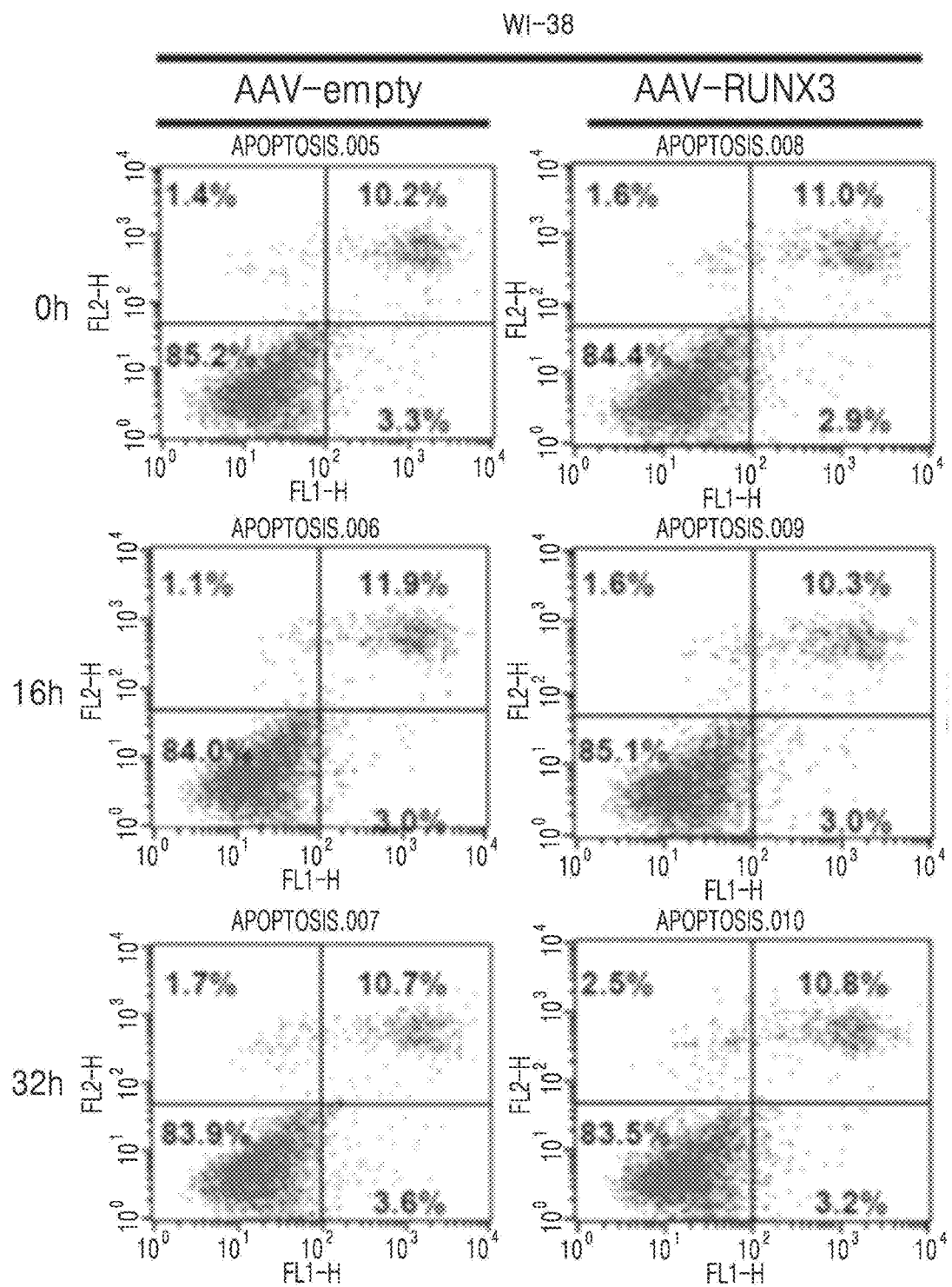
FIG. 6B shows results of a fluorescence-activated cell sorting (FACS) analysis, 0 hours (top), 16 hours (middle), and 32 hours (bottom) after infecting KRAS mutated lung cancer cell lines (H460, Calu6) and normal lung epithelial cells (WI38) with Example 1.

FIG. 6B shows results of a FACS analysis, 0 hours (top), 16 hours (middle), and 32 hours (bottom) after infecting normal lung epithelial cells (WI38) with Example 1.

Figure 6C:
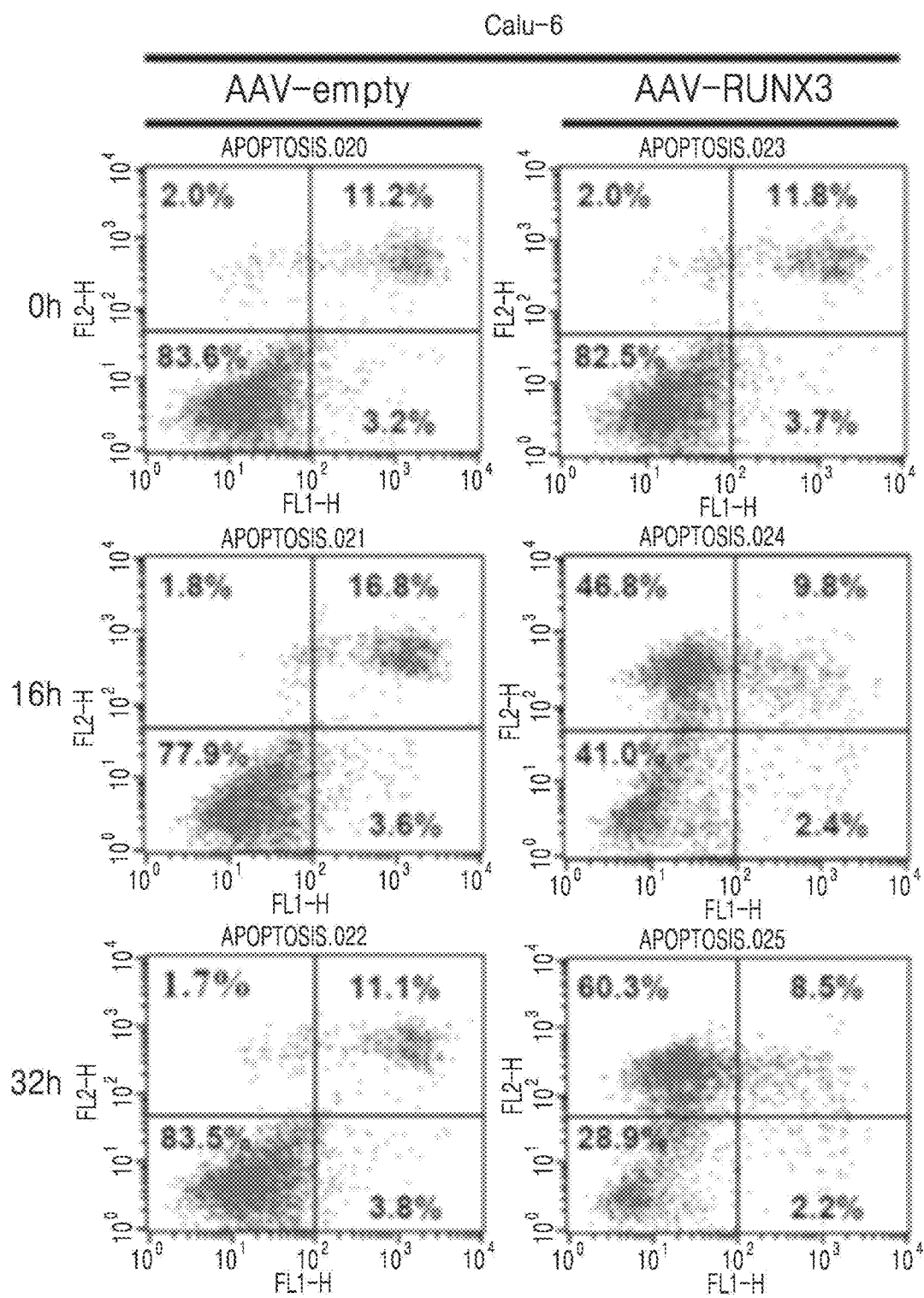
FIG. 6C shows results of a FACS analysis 0 hours (top), 16 hours (middle), and 32 hours (bottom) after infecting a KRAS mutated lung cancer cell line (Calu6) with Example 1.

FIG. 6C shows results of a FACS analysis 0 hours (top), 16 hours (middle), and 32 hours (bottom) after infecting a KRAS mutated lung cancer cell line (Calu6) with Example 1.

Figure 6D:
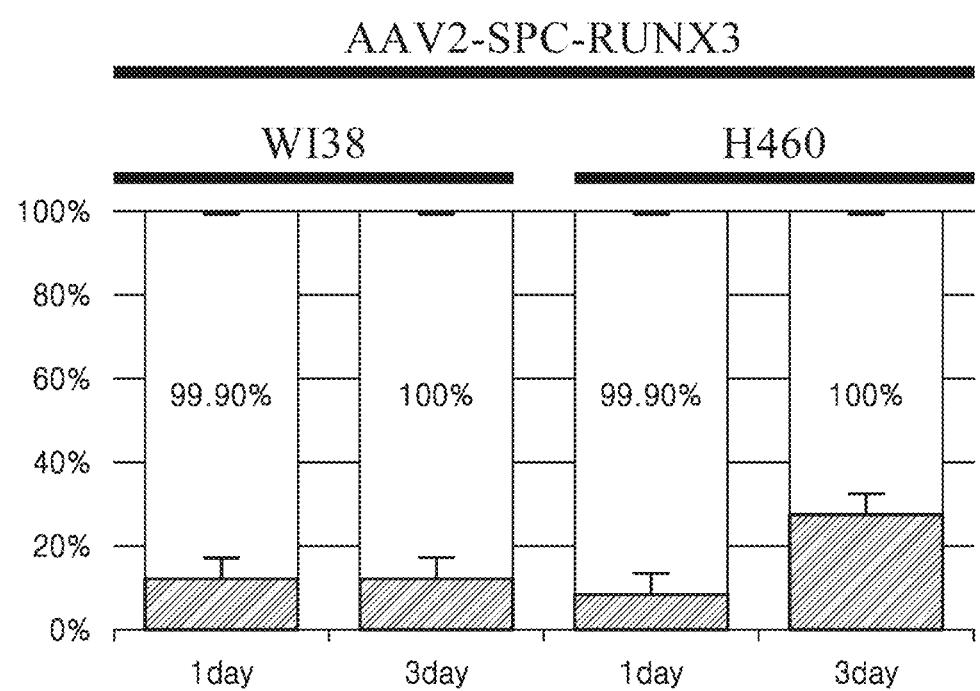
FIG. 6D shows a graph quantifying results of FACS analyses, 1 day and 3 days after infecting a KRAS mutated lung cancer cell line (H460) and normal lung epithelial cells (WI38) with Example 1.

FIG. 6D shows a graph quantifying results of FACS analyses, 1 day and 3 days after infecting a KRAS mutated lung cancer cell line (H460) and normal lung epithelial cells (WI38) with Example 1.

Figure 6E:
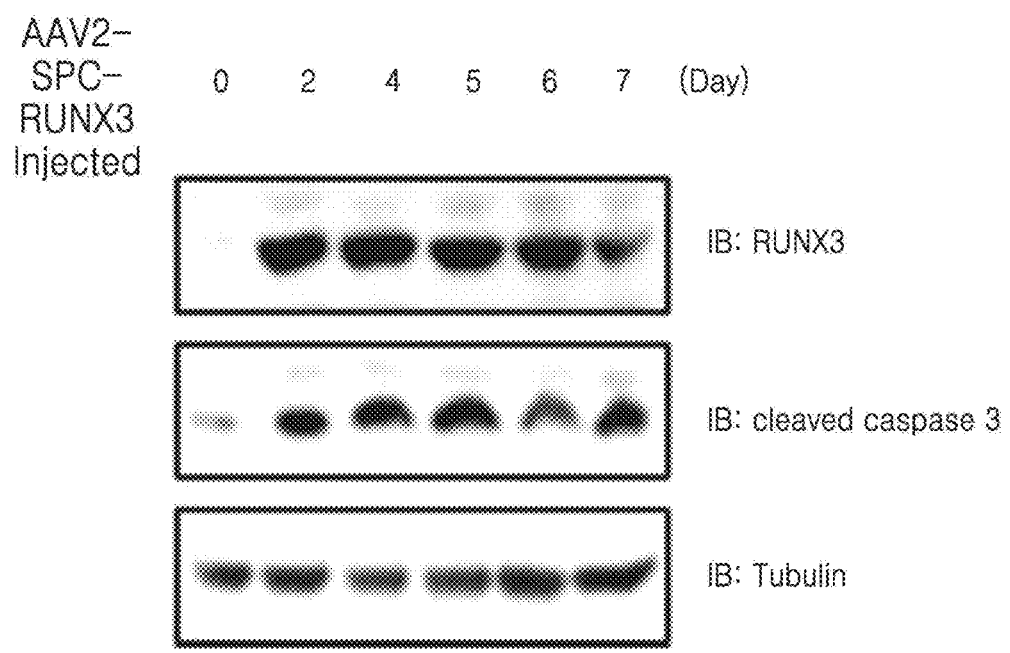
FIG. 6E shows results of detecting RUNX3 and cleaved caspase 3 expressed in KRAS mutated lung cancer cell lines infected with Example 1.

FIG. 6E shows results of detecting RUNX3 and cleaved caspase 3 expressed in KRAS mutated lung cancer cell lines infected with Example 1.

As a result, as shown in FIG. 6A, for the lung cancer cell line infected with the complex of Example 1, it was confirmed that most of the cells died on day 5 of infection. On the other hand, it was confirmed that no cell death was observed in normal lung epithelial cells.

In addition, as shown in FIGS. 6B to 6D, for the lung cancer cell line (H460) infected with the complex of Example 1, it was confirmed that a cell death rate increased by about 4 times or more on day 3 of infection compared to day 1 of infection. On the other hand, it was confirmed that there was no change in a cell death rate over time in normal lung epithelial cells (WI38).

In addition, as shown in FIG. 6E, for the lung cancer cell line infected with the complex of Example 1, it was confirmed that expression of RUNX3 and cleaved caspase 3 increased continuously from day 2 after infection.

That is, since the AAV complex according to an aspect is not toxic to normal cells and selectively kills only KRAS mutated lung cancer cell lines, it may be useful for preventing or treating KRAS mutated lung cancer.

3-3. Confirmation of Cancer Tissue Necrosis in Non-Small Cell Lung Cancer Xenograft Models A necrotic effect of the recombinant AAV complex according to an aspect on cancer tissues in non-small cell lung cancer xenograft models was confirmed. Specifically, non-small cell lung cancer cell line H460 was subcutaneously injected into the dorsal flank of 6-week-old nude mice at $2\times10^5$ cells/mice to prepare non-small cell lung cancer xenograft models. Example 1 was mixed and diluted with the same volume of PBS to $2\times10^7$ viral genome/mm$^3$. Thereafter, the xenograft model mice were bred for 2 weeks, and when a diameter of the subcutaneously transplanted cell mass reached about 5 mm to 10 mm, the diluted solution was directly injected into the cancer tissue. A control group was injected with a dilution of an AAV complex (AAV-empty) with a genome that did not include RUNX3. After the injection, the mice were bred for an additional 12 days, and when a cancer volume increased by an average of 100% or more compared to day 0, the mice were euthanized. Thereafter, the cancer tissue was removed from the mouse, and cut to show a cross section. The experiment was proceeded by using a total of eight mice, among which four mice (DI1, DI2, DI3, DI4) were injected with Example 1, and four mice (Con1, Con2, Con3, Con4) were injected with AAV-empty, under the same conditions.

Figure 7A:
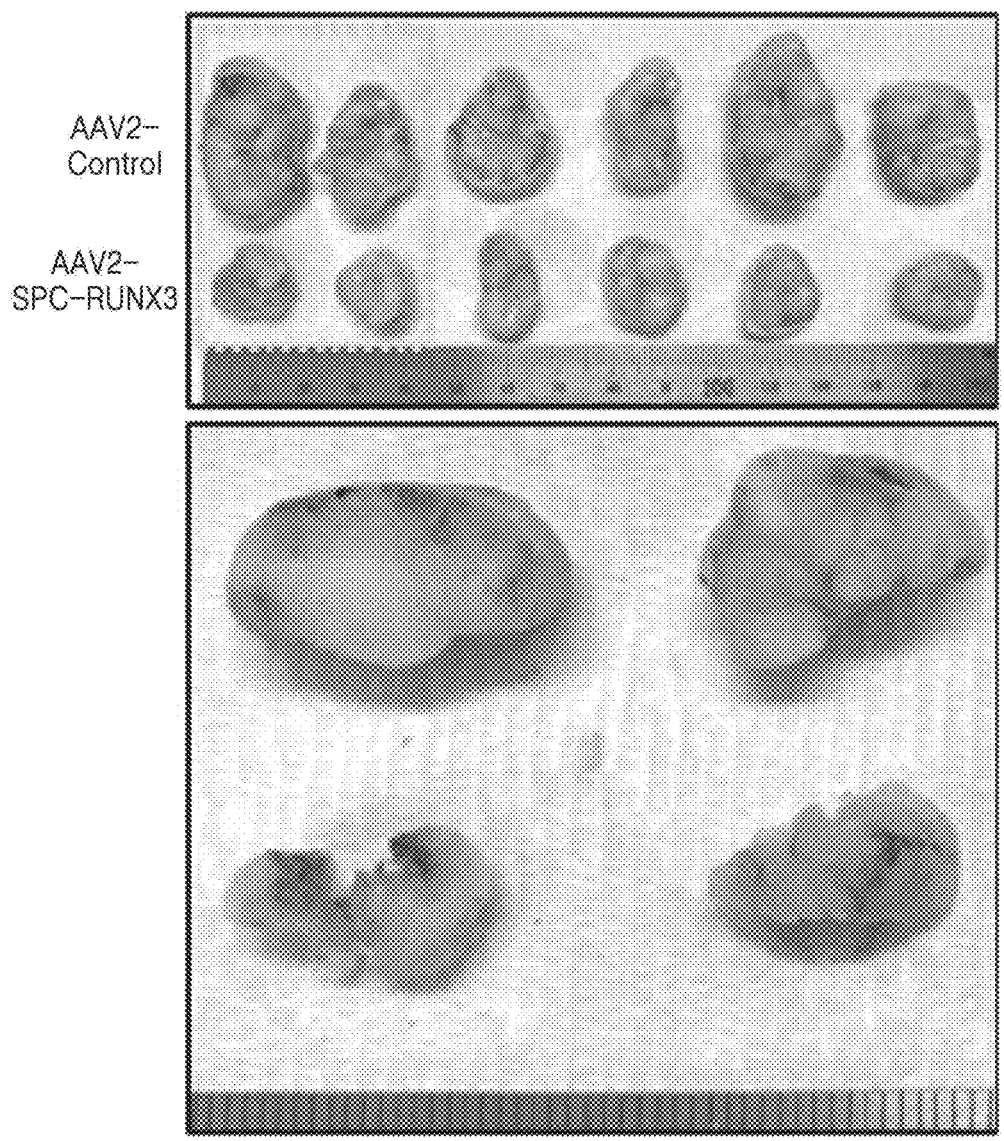
FIG. 7A shows results of confirming insides of cancer tissues cut to show cross sections, after injecting Example 1 into non-small cell lung cancer xenograft models and breeding for 12 days. AAV2-Control: injected with AAV having a genome that does not contain RUNX3 (AAV-empty), AAV2-SPC-RUNX3: injected with AAV complex of Example 1.

FIG. 7A shows results of confirming insides of cancer tissues cut to show cross sections, after injecting Example 1 into non-small cell lung cancer xenograft models and breeding for 12 days.

Figure 7B:
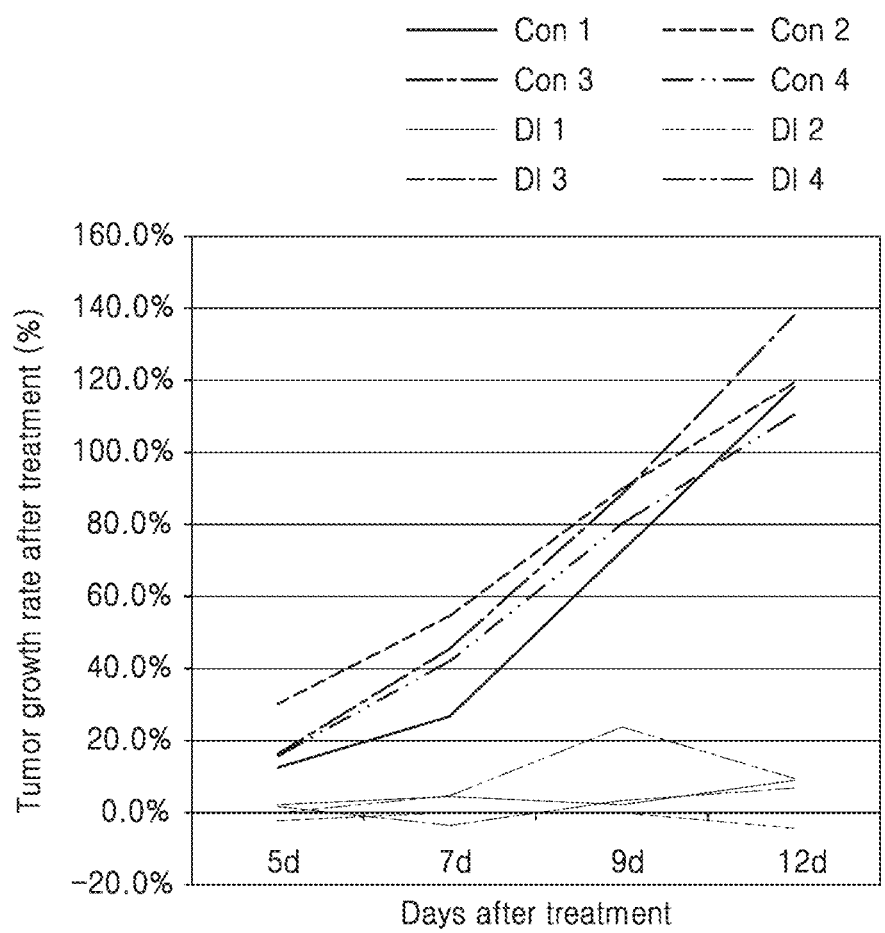
FIG. 7B shows results of measuring volumes of cancer tissues, after injecting Example 1 into non-small cell lung cancer xenograft models and breeding for 12 days; Con1~4: mice each treated with AAV-control (Empty), DI1~4: mice each treated with AAV2-SPC-RUNX3 (RX001).

FIG. 7B shows results of measuring volumes of cancer tissues, after injecting Example 1 into non-small cell lung cancer xenograft models and breeding for 12 days.

As a result, as shown in FIG. 7A, for the xenograft animal models injected with Example 1, it was confirmed that the cancer was necrotic or binding force of the cancer mass was loosely maintained, due to RUNX3.

In addition, as shown in FIG. 7B, for the xenograft animal models injected with Example 1, there was little change in the volume of cancer tissue until 12 days after injection. On the other hand, for the control group, it was confirmed that a volume of the cancer tissue increased by up to 150% on day 12 after injection, compared to day 1.

That is, the AAV complex according to an aspect expresses the RUNX3 gene specifically for lung cancer, thereby inhibiting tumor growth and inducing cell death by the RUNX3 gene, and thus, the AAV complex may be useful for preventing or treating KRAS mutated lung cancer.

The above description of the present disclosure is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

The adeno-associated virus complex according to an aspect has asymmetric ITRs in which one of the two ITRs is modified, thereby increasing self-replication efficiency in host cells and increasing expression efficiency of a delivered gene, and therefore, compared to existing AAV complexes, the adeno-associated virus complex has an advantage of improved productivity and gene expression efficiency.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An adeno-associated virus (AAV) complex, comprising a polynucleotide sequence encoding a runt-related transcription factor 3 (RUNX3) protein between a first inverted terminal repeat (ITR) and a second ITR,
   wherein the first ITR is not modified and the second ITR is modified, and
   wherein the second ITR, all or part of a stem-loop structure, which is formed of rep-binding element (RBE), RBE', A, A', B, B', C, C', and D regions, is modified.

2. The adeno-associated virus complex of claim 1, comprising: an operably linked SPC promoter, a polynucleotide sequence encoding a RUNX3 protein, and a polyadenylation sequence, between the first ITR and the second ITR.

3. The adeno-associated virus complex of claim 1, wherein AAV is of an AAV serotype selected from the group consisting of AAV1, AAV2, AAV3, AAV4, AAV5, AAV6, AAV7, AAV8, AAV9, AAV10, AAV11, and AAV12.

4. The adeno-associated virus complex of claim 1, wherein the modification of the stem-loop structure is insertion, deletion, or substitution.

5. The adeno-associated virus complex of claim 1, wherein the second ITR is modified to not form a stem-loop structure.

6. The adeno-associated virus complex of claim 1, wherein the second ITR, all or part of a stem-loop structure, which is formed of rep-binding element (RBE), RBE', A, A', B, B', C, C', and D regions, is deleted.

7. The adeno-associated virus complex of claim 1, wherein the second ITR comprises a terminal resolution site (trs) sequence and an RBE sequence, and has deleted therefrom all of C, C', B', B, RBE', A' and D sequences after RBE.

8. The adeno-associated virus complex of claim 1, wherein the first ITR is an AAV wild-type ITR, and the second ITR consists essentially of a nucleotide sequence selected from the group consisting of SEQ ID NOs: 1 to 9.

9. The adeno-associated virus complex of claim 1, wherein the first ITR is an AAV wild-type ITR, and the second ITR consists essentially of a nucleotide sequence of SEQ ID NO: 1.

10. The adeno-associated virus complex of claim 1, further comprising a gene junction comprising SEQ ID NO: 10 between the SPC promoter and the nucleotide sequence encoding RUNX3.

11. A method of treating KRAS mutated lung cancer, comprising administering an effective amount of the adeno-associated virus complex of claim 1 to a subject in need thereof.

12. The method of claim 11, wherein the lung cancer is non-small cell lung cancer.

13. The method of claim 12, wherein the non-small cell lung cancer is selected from the group consisting of squamous cell carcinoma, large cell carcinoma, and lung adenocarcinoma.

14. A pharmaceutical composition for preventing or treating KRAS mutated lung cancer, comprising the adeno-associated virus complex of claim 1 and a pharmaceutically acceptable carrier.

* * * * *

SEQUENCE LISTING

```
Sequence total quantity: 22
SEQ ID NO: 1              moltype = DNA   length = 58
FEATURE                   Location/Qualifiers
source                    1..58
                          mol_type = genomic DNA
                          organism = Adeno-associated virus 2
SEQUENCE: 1
aggaacccct agtgatggag ttggccactc cctctctgcg cgctcgctcg ctcactga       58

SEQ ID NO: 2              moltype = DNA   length = 56
FEATURE                   Location/Qualifiers
source                    1..56
                          mol_type = genomic DNA
                          organism = Adeno-associated virus 1
SEQUENCE: 2
ttacccctag tgatggagtt gcccactccc tctccgcgcg ctcgctcgct cggtgg         56

SEQ ID NO: 3              moltype = DNA   length = 56
FEATURE                   Location/Qualifiers
source                    1..56
                          mol_type = genomic DNA
                          organism = Adeno-associated virus 3
SEQUENCE: 3
atacctctag tgatggagtt ggccactccc tctatgcgca ctccctcgct gggtgg         56

SEQ ID NO: 4              moltype = DNA   length = 58
FEATURE                   Location/Qualifiers
source                    1..58
                          mol_type = genomic DNA
                          organism = Adeno-associated virus 4
SEQUENCE: 4
ggcaaaccta gatgatggag ttggccactc cctctatgcg cgctcgctca ctcactcg       58

SEQ ID NO: 5              moltype = DNA   length = 56
FEATURE                   Location/Qualifiers
source                    1..56
                          mol_type = genomic DNA
                          organism = Adeno-associated virus 6
SEQUENCE: 5
ataccctag tgatggagtt gcccactccc tctatgcgcg ctcgctcgct cggtgg          56

SEQ ID NO: 6              moltype = DNA   length = 58
FEATURE                   Location/Qualifiers
source                    1..58
                          mol_type = genomic DNA
                          organism = Adeno-associated virus 7
SEQUENCE: 6
cggtacccct agtgagggag ttggccactc cctctatgcg cgctcgctcg ctcggtgg       58

SEQ ID NO: 7              moltype = DNA   length = 68
FEATURE                   Location/Qualifiers
source                    1..68
                          mol_type = genomic DNA
                          organism = Adeno-associated virus 5
SEQUENCE: 7
aaaacctcct tgcttgagag tgtggcactc tcccccctgt cgcgttcgcg cgctcgctgg     60
ctcgtttg                                                              68

SEQ ID NO: 8              moltype = DNA   length = 57
FEATURE                   Location/Qualifiers
source                    1..57
                          mol_type = genomic DNA
                          organism = Adeno-associated virus 8
SEQUENCE: 8
ggatctcggg gttccagcgc ttgctgtttt ccttctgcag ctcccattca atttcca        57

SEQ ID NO: 9              moltype = DNA   length = 57
FEATURE                   Location/Qualifiers
source                    1..57
                          mol_type = genomic DNA
                          organism = Adeno-associated virus 9
SEQUENCE: 9
ggatctctgg attccagcgc ttgctgtttt ctttctgcag ctcccactcg atttcca        57

SEQ ID NO: 10             moltype = DNA   length = 27
FEATURE                   Location/Qualifiers
source                    1..27
                          mol_type = other DNA
```

```
                        organism = synthetic construct
SEQUENCE: 10
tatatcacta gtggtaccgc ggccacc                                              27

SEQ ID NO: 11           moltype = DNA   length = 33
FEATURE                 Location/Qualifiers
source                  1..33
                        mol_type = other DNA
                        organism = synthetic construct
SEQUENCE: 11
tggtaccgcg gccaccatgc gtattcccgt aga                                       33

SEQ ID NO: 12           moltype = DNA   length = 31
FEATURE                 Location/Qualifiers
source                  1..31
                        mol_type = other DNA
                        organism = synthetic construct
SEQUENCE: 12
aagctttact cgagtcagta gggccgccac a                                         31

SEQ ID NO: 13           moltype = DNA   length = 18
FEATURE                 Location/Qualifiers
source                  1..18
                        mol_type = other DNA
                        organism = synthetic construct
SEQUENCE: 13
ctgctagcag aaggcagc                                                        18

SEQ ID NO: 14           moltype = DNA   length = 32
FEATURE                 Location/Qualifiers
source                  1..32
                        mol_type = other DNA
                        organism = synthetic construct
SEQUENCE: 14
ggtaccacta gtgatatctt ttgtaaggtt tc                                        32

SEQ ID NO: 15           moltype = DNA   length = 39
FEATURE                 Location/Qualifiers
source                  1..39
                        mol_type = other DNA
                        organism = synthetic construct
SEQUENCE: 15
tgtatccgct catgagagct cggtcatagc tgtttcctg                                 39

SEQ ID NO: 16           moltype = DNA   length = 40
FEATURE                 Location/Qualifiers
source                  1..40
                        mol_type = other DNA
                        organism = synthetic construct
SEQUENCE: 16
ggattttggt catgagcatg cttagaaaaa ctcatcgagc                                40

SEQ ID NO: 17           moltype = DNA   length = 25
FEATURE                 Location/Qualifiers
source                  1..25
                        mol_type = other DNA
                        organism = synthetic construct
misc_feature
                        note = Phosphorylation
SEQUENCE: 17
cactgactcg ctgcgctcgg tcgtt                                                25

SEQ ID NO: 18           moltype = DNA   length = 25
FEATURE                 Location/Qualifiers
source                  1..25
                        mol_type = other DNA
                        organism = synthetic construct
misc_feature
                        note = Phosphorylation
SEQUENCE: 18
agcgagtcag tgagcgagcg agcgc                                                25

SEQ ID NO: 19           moltype = AA    length = 429
FEATURE                 Location/Qualifiers
source                  1..429
                        mol_type = protein
                        organism = Homo sapiens
SEQUENCE: 19
MASNSIFDSF PTYSPTFIRD PSTSRRFTPP SPAFPCGGGG GKMGENSGAL SAQAAVGPGG           60
```

```
RARPEVRSMV DVLADHAGEL VRTDSPNFLC SVLPSHWRCN KTLPVAFKVV ALGDVPDGTV    120
VTVMAGNDEN YSAELRNASA VMKNQVARFN DLRFVGRSGR GKSFTLTITV FTNPTQVATY    180
HRAIKVTVDG PREPRRHRQK LEDQTKPFPD RFGDLERLRM RVTPSTPSPR GSLSTTSHFS    240
SQPQTPIQGT SELNPFSDPR QFDRSFPTLP TLTESRFPDP RMHYPGAMSA AFPYSATPSG    300
TSISSLSVAG MPATSRFHHT YLPPPYPGAP QNQSGPFQAN PSPYHLYYGT SSGSYQFSMV    360
AGSSSGGDRS PTRMLASCTS SAASVAAGNL MNPSLGGQSD GVEADGSHSN SPTALSTPGR    420
MDEAVWRPY                                                           429

SEQ ID NO: 20          moltype = AA   length = 415
FEATURE                Location/Qualifiers
source                 1..415
                       mol_type = protein
                       organism = Homo sapiens
SEQUENCE: 20
MRIPVDPSTS RRFTPPSPAF PCGGGGGKMG ENSGALSAQA AVGPGGRARP EVRSMVDVLA     60
DHAGELVRTD SPNFLCSVLP SHWRCNKTLP VAFKVVALGD VPDGTVVTVM AGNDENYSAE    120
LRNASAVMKN QVARFNDLRF VGRSGRGKSF TLTITVFTNP TQVATYHRAI KVTVDGPREP    180
RRHRQKLEDQ TKPFPDRFGD LERLRMRVTP STPSPRGSLS TTSHFSSQPQ TPIQGTSELN    240
PFSDPRQFDR SFPTLPTLTE SRFPDPRMHY PGAMSAAFPY SATPSGTSIS SLSVAGMPAT    300
SRFHHTYLPP PYPGAPQNQS GPFQANPSPY HLYYGTSSGS YQFSMVAGSS SGGDRSPTRM    360
LASCTSSAAS VAAGNLMNPS LGGQSDGVEA DGSHSNSPTA LSTPGRMDEA VWRPY         415

SEQ ID NO: 21          moltype = DNA   length = 1380
FEATURE                Location/Qualifiers
source                 1..1380
                       mol_type = genomic DNA
                       organism = Homo sapiens
SEQUENCE: 21
gccttcttca gagcggggca tggcatcgaa cagcatcttc gactccttcc cgacctactc     60
gccgaccttc atccgcgacc caagcaccag ccgccgcttc acacctccct ccccggcctt    120
cccctgcggc ggcggcggcg gcaagatggg cgagaacagc ggcgcgctga gcgcgcaggc    180
ggccgtgggg cccggagggc gcgcccggcc cgaggtgcgc tcgatggtgg acgtgctggc    240
ggaccacgca ggcgagctcg tgcgcaccga cagccccaac ttcctctgct ccgtgctgcc    300
ctcgcactgg cgctgcaaca gacgctgccg cgtcgccttc aaggtggtgg cattggggga    360
cgtgccggat ggtacggtgg tgactgtgat ggcaggcaat gacgagaact actccgctga    420
gctgcgcaat gcctcggccg tcatgaagaa ccaggtggcc aggttcaacg accttcgctt    480
cgtgggccgc agtgggcgag ggaagagttt caccctgacc atcactgtgt tcaccaaccc    540
cacccaagtg gcgacctacc accgagccat caaggtgacc gtggacggac cccgggagcc    600
cagacggcac cggcagaagc tggaggacca gaccaagccg ttccctgacc gctttgggga    660
cctgaaacgg ctgcgcatgc gggtgacacc gagcacaccc agccccgag gctcactcag    720
caccacaagc cacttcagca gccagcccca gaccccaatc caaggcacct cggaactgaa    780
cccattctcc gaccccgcc agtttgaccg ctccttcccc acgctgccaa ccctcacgga    840
gagccgcttc ccagacccca ggatgcatta tcccggggcc atgtcagctg ccttcccta     900
cagcgccacg ccctcgggca cgagcatcag cagcctcagc gtggcgggca tgccggccac    960
cagccgcttc accataccct acctcccgcc acctacccgg ggcccccgc agaaccagag   1020
cgggccctt caggccaacc cgtcccccta ccacctctac tacgggacat cctctggctc   1080
ctaccagttc tccatggtgg ccggcagcag cagtgggggc gaccgctcac ctacccgcat   1140
gctggcctct tgcaccagca gcgctgcctc tgtcgccgcc ggcaacctca tgaacccag    1200
cctgggcggc cagagtgatg gcgtggaggc cgacggcagc cacagcaact acccacggc    1260
cctgagcacg ccaggccgca tggatgaggc cgtgtggcgg ccctactgac cgccctggtg   1320
gactcctccc gctggaggcg ggaccctaa caaccttcaa gaccagtgat gggccggtc     1380

SEQ ID NO: 22          moltype = DNA   length = 1320
FEATURE                Location/Qualifiers
source                 1..1320
                       mol_type = genomic DNA
                       organism = Homo sapiens
SEQUENCE: 22
cggggaagc gcgccgtct ccgcctgccc ggcgccctga cggccgctgt tatgcgtatt       60
cccgtagacc caagcaccag ccgccgcttc acacctccct ccccggcctt cccctgcggc    120
ggcggcggcg gcaagatggg cgagaacagc ggcgcgctga gcgcgcaggc ggccgtgggg    180
cccggagggc gcgcccggcc cgaggtgcgc tcgatggtgg acgtgctggc ggaccacgca    240
ggcgagctcg tgcgcaccga cagccccaac ttcctctgct ccgtgctgcc ctcgcactgg    300
cgctgcaaca gacgctgccg cgtcgccttc aaggtggtgg cattggggga cgtgccggat    360
ggtacggtgg tgactgtgat ggcaggcaat gacgagaact actccgctga gctgcgcaat    420
gcctcggccg tcatgaagaa ccaggtggcc aggttcaacg accttcgctt cgtgggccgc    480
agtgggcgag ggaagagttt caccctgacc atcactgtgt tcaccaaccc cacccaagtg    540
gcgacctacc accgagccat caaggtgacc gtggacggac cccgggagcc cagacggcac    600
cggcagaagc tggaggacca gaccaagccg ttccctgacc gctttgggga cctgaacgg     660
ctgcgcatgc gggtgacacc gagcacaccc agccccgag gctcactcag caccacaagc    720
cacttcagca gccagcccca gaccccaatc caaggcacct cggaactgaa cccattctcc    780
gaccccgcc agtttgaccg ctccttcccc acgctgccaa ccctcacgga gagccgcttc    840
ccagacccca ggatgcatta tcccggggcc atgtcagctg ccttccccta cagcgccacg    900
ccctcgggca cgagcatcag cagcctcagc gtggcgggca tgccggccac cagccgcttc    960
accataccct acctcccgcc acctacccg ggcccccgc agaaccagag cgggccctt     1020
caggccaacc cgtcccccta ccacctctac tacgggacat cctctggctc ctaccagttc   1080
tccatggtgg ccggcagcag cagtgggggc gaccgctcac ctacccgcat gctggcctct   1140
```

```
tgcaccagca gcgctgcctc tgtcgccgcc ggcaacctca tgaacccag  cctgggcggc  1200
cagagtgatg gcgtggaggc cgacggcagc cacagcaact cacccacggc cctgagcacg  1260
ccaggccgca tggatgaggc cgtgtggcgg ccctactgac cgccctggtg gactcctccc  1320
```